US008597351B2

(12) United States Patent
Rathert

(10) Patent No.: US 8,597,351 B2
(45) Date of Patent: Dec. 3, 2013

(54) HOLDING DEVICE FOR AN INTRAOCULAR LENS, PACKAGING AND TRANSPORT MEANS FOR AN INTRAOCULAR LENS, INJECTOR DEVICE FOR AN INTRAOCULAR LENS AS WELL AS METHOD FOR PACKAGING AN INTRAOCULAR LENS AND METHOD FOR LOADING AN INTRAOCULAR LENS INTO AN INJECTOR DEVICE

(75) Inventor: Brian Rathert, Berlin (DE)

(73) Assignee: Carl Zeiss Meditec SAS, La Rochelle Cedex (FR)

( * ) Notice: Subject to any disclaimer, the term of this patent is extended or adjusted under 35 U.S.C. 154(b) by 95 days.

(21) Appl. No.: 12/858,267

(22) Filed: Aug. 17, 2010

(65) Prior Publication Data
US 2011/0046634 A1 Feb. 24, 2011

(30) Foreign Application Priority Data

Aug. 18, 2009 (GB) .................................. 0915098.8

(51) Int. Cl.
*A61F 2/16* (2006.01)
(52) U.S. Cl.
USPC ......................................... 623/6.12; 606/107
(58) Field of Classification Search
USPC ............ 606/107, 166, 1; 623/6.11, 6.12, 6.18
See application file for complete search history.

(56) References Cited

U.S. PATENT DOCUMENTS

| 5,275,604 A | 1/1994 | Rheinish et al. |
| 5,468,246 A | 11/1995 | Blake |
| 5,582,614 A | 12/1996 | Feingold |
| 5,817,075 A * | 10/1998 | Giungo ......................... 604/294 |
| 6,386,357 B1 * | 5/2002 | Egawa ........................... 206/5.1 |
| 6,468,282 B2 | 10/2002 | Kikuchi et al. |
| 6,712,848 B1 * | 3/2004 | Wolf et al. .................... 623/6.12 |
| 2002/0077633 A1 | 6/2002 | Kikuchi et al. |
| 2005/0125000 A1 | 6/2005 | Tourrette et al. |
| 2007/0150055 A1 | 6/2007 | Pynson |
| 2008/0058830 A1 | 3/2008 | Cole et al. |
| 2008/0119865 A1 | 5/2008 | Meunier et al. |
| 2008/0269770 A1 | 10/2008 | Pynson et al. |

FOREIGN PATENT DOCUMENTS

| DE | 10015472 A1 | 10/2001 |
| EP | 1042999 A1 | 10/2000 |
| EP | 0 722 292 B1 | 7/2003 |

(Continued)

OTHER PUBLICATIONS

European Search Report, European Patent Application No. 10172666.9, date of completion of the search Dec. 10, 2010, 6 pages (corresponds to U.S. Appl. No. 12/858,227).

(Continued)

*Primary Examiner* — Victor Nguyen
(74) *Attorney, Agent, or Firm* — Fitch, Even, Tabin & Flannery LLP

(57) ABSTRACT

The invention relates to a holding device for an intraocular lens, characterized in that the holding device has an elongated support member open to the bottom, on which an elongated holding rail for holding the lens is disposed. The invention also relates to an injector device for an intraocular lens as well as to a packaging and transport device for the intraocular lens. Furthermore, the invention relates to a method for packaging an intraocular lens as well as to a method for loading an intraocular lens into an injector device.

16 Claims, 16 Drawing Sheets

(56) References Cited

FOREIGN PATENT DOCUMENTS

| | | |
|---|---|---|
| EP | 1360944 A2 | 11/2003 |
| EP | 1961399 A1 | 8/2008 |
| EP | 1972306 A1 | 9/2008 |
| EP | 1 233 730 B1 | 4/2009 |
| EP | 2074961 A1 | 7/2009 |
| WO | 88/01142 A1 | 2/1988 |
| WO | 95/24863 A1 | 9/1995 |
| WO | 96/03924 A1 | 2/1996 |
| WO | 97/13476 A1 | 4/1997 |
| WO | 00/62713 A1 | 10/2000 |
| WO | 01/39701 A1 | 6/2001 |
| WO | 01/87187 A1 | 11/2001 |
| WO | 2005/023154 A2 | 3/2005 |
| WO | 2006/070561 A1 | 7/2006 |
| WO | 2007/078603 A2 | 7/2007 |
| WO | 2009029472 A1 | 3/2009 |

OTHER PUBLICATIONS

European Search Report, European Patent Application No. 10172664.4, date of completion of the search Dec. 22, 2010, 7 pages (corresponds to U.S. Appl. No. 12/858,267).

European Search Report, European Patent Application No. 10172668.5, date of completion of the search Dec. 23, 2010, 7 pages (corresponds to U.S. Appl. No. 12/858,280).

* cited by examiner

HOLDING DEVICE FOR AN INTRAOCULAR LENS, PACKAGING AND TRANSPORT MEANS FOR AN INTRAOCULAR LENS, INJECTOR DEVICE FOR AN INTRAOCULAR LENS AS WELL AS METHOD FOR PACKAGING AN INTRAOCULAR LENS AND METHOD FOR LOADING AN INTRAOCULAR LENS INTO AN INJECTOR DEVICE

CROSS-REFERENCE TO RELATED APPLICATION

This application claims foreign priority 35 U.S.C. §119 to British Patent Application No. 0915098.8, filed Aug. 18, 2009, which is hereby incorporated herein by reference in its entirety.

TECHNICAL FIELD

The invention relates to a holding device for an intraocular lens as well as to a packaging and transport means for an intraocular lens. Furthermore, the invention relates to an injector device for an intraocular lens. Moreover, the invention includes a method for packaging an intraocular lens as well as a method for loading an intraocular lens into an injector device.

PRIOR ART

From the prior art, both holding devices for an intraocular lens and injector devices as well as packaging and transport means for an intraocular lens are known. For example, intraocular lenses are inserted into the eye as a substitute for the natural lens of the eye, if the natural lens is damaged or the vision of the eye is impaired. For example, the natural lens can be removed from the eye by fragmentation and suction. The intraocular lens can be introduced with the injector device through a small incision on the eye. Typically, an intraocular lens includes an optic part as well as haptic parts disposed thereon, with which the intraocular lens is positionable in the desired position in the eye. For introducing the intraocular lens through a small incision in the eye, it is preferably provided that the lens is folded or rolled, wherein this is in particular already effected in the injector device. In the eye, the lens is then brought into its original shape and positioned.

Typically, the intraocular lens is provided in a packaging and transport means and so delivered to a physician or other medical personnel. The intraocular lens is protected during handling and transport by the packaging and transport means. Such packaging and transport means are known, in which the lens is only inserted in the transport container in a sterile liquid inputted therein in simple manner. With these means, the medical personnel then has to remove the lens from the transport container and to insert it into the injector device with additional auxiliary means or auxiliary tools, respectively, such as for example forceps or the like, before the surgical procedure. In this approach, thus, the transfer from the transport container into a loading chamber of the injector device is performed with an auxiliary tool. In elaborate and error-prone manner, introduction into the loading chamber has to be made by operation of the forceps, which is manifold individual to user in character. Such an operation demands a relatively high amount of dexterity and experience and can result in the intraocular lens being erroneously loaded into the injector. Moreover, by this increased manual handling, the risk is increased that the intraocular lens and/or the injector device are damaged or contaminated.

From EP 1 173 115 B1, a holding device for an intraocular lens as well as an injection device and a packaging system for an intraocular lens are known. The holding device is designed relatively elaborate and presents a closed cassette, into which a support rail, on which the intraocular lens is disposed, can be introduced. Thus, the intraocular lens is disposed in the interior of the box. For insertion into the injector device, first, the cassette has to be opened, the support rail has to be removed and to be inserted into an injector. Here too, it is provided that the intraocular lens has to be removed from the holding part or the support rail, respectively, by means of an auxiliary tool in the form of forceps, in order to ensure the insertion into the eye. In another implementation, it can be provided that wing-like cover flaps of the injector device are joined by explicit manual grasping by a user, and thereby the lens is removable from the holding part. This approach is error-prone and can result in undesired positional displacements of the lens and in undesired folding events due to the direct controllability of the movement of these wings by the user. Therefore, here too, an operation, which is manifold individual to user in character, is required, which is disadvantageous.

Furthermore, from U.S. Pat. No. 6,468,282 B2, an injector device for an intraocular lens is known. With regard to user friendliness and simple handling, it has corresponding disadvantages, too.

Furthermore, it is known that such eye implants such as intraocular lenses as well as the injector device must be sterilized.

The implants and the injectors must be sterilized by means appropriate to the materials from which they are made. At present, certain hydrophilic acrylic intraocular implants are sterilized in an aqueous solution by steam sterilization in an autoclave. At present, other implants, and in particular PMMA, hydrophobic acrylic, silicone, and bimaterial (PMMA and hydrophobic acrylic) lenses, are sterilized with ethylene oxide (ETO). Others, and in particular bimaterial (PMMA and hydrophilic acrylic) implants, must be sterilized by irradiation with gamma rays.

Prior to steam sterilization in an autoclave, the intraocular implant is placed in a flask containing an aqueous saline solution and is then sealed hermetically before it is placed in the autoclave. The flask serves as container or packaging for the implant.

The same applies to sterilization by gamma radiation, i.e. the intraocular implant is placed in a flask containing an aqueous solution which is hermetically sealed before undergoing irradiation.

Finally, hydrophobic acrylic and bimaterial (PMMA and hydrophobic acrylic) or silicone implants are sterilized dry in a container that is permeable to ethylene oxide and then packaged dry in a container of appropriate shape. If the implant is made from silicone or hydrophobic acrylic, the combination of the implant, the body of the injector, and the canula attached to the injector may be sterilized with ETO. However, this kind of combination has a limited shelf life. This is because the canula contains, beneath the interior wall, a lubricant such as glycerol stearate, derivatives of polyamide, fatty alcohol polyethoxyethers, polyol ester, or ethoxylated amines, co-molded with the material from which the canula is made. After a limited time, the lubricant that initially impregnated the material of the canula migrates onto the surface of the interior wall of the canula in quantities such that the implant is covered with lubricant on passing through the canula, which affects its transparency and introduces lubricant residues into the eye.

In the case of hydrophilic acrylic or bimaterial implant, the implant and the combination of the injector body and the canula, or the canula only, may not be sterilized with the packaging, which is typically made of polypropylene, since the canula may not be sterilized at high temperature in an autoclave and this kind of implant may not be sterilized with ETO.

PRESENTATION OF THE INVENTION

It is the object of the present invention to provide a holding device for an intraocular lens as well as an injector device for an intraocular lens and a packaging and transport means for an intraocular lens. Furthermore, a method for packaging an intraocular lens as well as a method for loading an intraocular lens into an injector device are to be provided. Both the devices, the means and the methods are to be configured such that the high requirements to the sterilization can be satisfied and undesired damages of components can be avoided. Moreover, the manageability of the intraocular lens both in packaging and in transport and in the removal from the packaging and in performing the surgical procedure are to be improved and the user friendliness is to be increased.

These objects are solved by a holding device having at least some of the features described herein, a packaging and transport means having at least some of the features described herein, an injector device having at least some of the features described herein, and methods having at least some of the features described herein.

A holding device for an intraocular lens according to the invention includes a support member formed open to the bottom and moreover extending in elongated shape. Moreover, the holding device includes a holding rail for holding the intraocular lens, which is disposed on the elongated support member. With regard to the elongated configuration, in particular, the support member is formed longer in its longitudinal extension than its width. With respect to that, the support member is also designed rail-like, wherein the elongated holding rail is moreover also formed open to the bottom. Particularly, at least in certain regions, in cross-section, the support member is formed with an inverted U shape open to the bottom. The retention of the intraocular lens can thereby be improved and the accessibility to the intraocular lens is thereby simple and more user-friendly. By this configuration, it is no longer required that for inserting the intraocular lens into a loading chamber of the injector device, first, a case has to be opened in elaborate manner, in which a holding part for the intraocular lens is disposed with this lens. Thus, the holding device can be taken directly as it is configured and be connected to an injector device in order to be able to load the intraocular lens into the loading chamber of the injector device.

Preferably, the support member and the holding rail are movable relatively to each other. Thereby, the loading operation of the intraocular lens into the injector device can be configured still more functional and more simple, wherein, moreover, the more precise positioning in the loading chamber on the one hand and the removal of the intraocular lens from the holding rail on the other hand can also be simpler achieved.

Preferably, the holding rail is movable upwards and downwards along or parallel to the longitudinal axis of the support member and/or perpendicularly to the longitudinal axis. The different and manifold degrees of freedom of the mobility of the holding rail relatively to the support member again considerably promote the manageability of the holding device upon use on an injector device. Undesired positionings of the intraocular lens or undesired detachment of the intraocular lens from the holding rail can thereby be avoided in the insertion operation into the loading chamber of the injector device.

Preferably, in its loading position on the holding rail, the lens is disposed on a bottom side of the holding rail and positioned freely accessible through the support member open at the bottom. This configuration too, allows the secure retention of the intraocular lens on the holding device on the one hand and the simple removal of the intraocular lens from the holding rail on the other hand if this is required. Preferably, in its loading position on the holding rail, the lens is freely accessible on both sides laterally and from below. Considered in longitudinal direction of the support member, preferably, the intraocular lens is only retained on a front side and a rear side on the holding rail such that the free accessibility is provided otherwise. Thereby too, a particularly advantageous functional principle with regard to automatic introduction of the intraocular lens into the loading chamber of the injector device can be promoted. Besides the holding device, thus, additional auxiliary tools such as forceps or the like are no longer required. Thereby, undesired contamination can be avoided on the one hand and undesired manual operations by the user upon insertion operation can be reduced on the other hand. The insertion of the intraocular lens into the loading chamber of the injector device in undesired erroneous positions can thereby be avoided.

Preferably, the support member has at least one gripping member on the top or the outer side. By this configuration, simple accessibility can be provided to a user for gripping, whereby the entire holding device can quickly and unerringly be held and moved.

Preferably, the support member has a base body open to the bottom, on which support arms extending parallel to the longitudinal axis and are respectively disposed on opposing sides of the longitudinal axis of the support member. This constructive configuration of the support member allows a very open structure on the one hand such that the accessibility is provided from many sides, and provides a highly-functional part on the other hand, which moreover is formed reduced in weight.

Preferably, at least one guide member is disposed on each support arm on the facing interior sides of the support arms. Each guide member is formed for engagement with a cover flap of an injector device covering a receiving space. By this automatic mechanic possibility of coupling between the guide members and the cover flaps, automatic operation of the cover flaps can be achieved if the holding device is mechanically coupled to the injector device. Upon introduction of the intraocular lens into the loading chamber of the injector device, thus, it is no longer required that a user directly has to explicitly manually grasp these cover flaps and to move them in order to be able to achieve closure. Thus, by this configuration of the holding device, the introduction of the intraocular lens into the loading chamber virtually contactless on the part of the user on the one hand, and additionally the automatic closure of the cover flaps of the injector device are achieved automatically, without a user having to explicitly grasp these cover flaps. Thus, a highly functional and matched motion sequence is performed automatically, which manages several operations. Thus, by the holding device, virtually a self-closing configuration of the cover flaps of the injector device can be achieved, and autonomous automatic removal of the intraocular lens from the holding rail can be allowed.

Preferably, on a lower border of the base body of the support member and/or on a lower border of at least one support arm, a positioning member is disposed, by which the holding device is fixedly attachable in a transport container. By this configuration, it is ensured that the intraocular lens is no longer inserted in the transport container in unprotected and virtually freely movable manner. Just for packaging and transporting the intraocular lens, thus, an additional protection for the lens is ensured by this specification of the holding device. The lens is attached to the holding device and the holding device is disposed in the transport container in positionally stable manner. Even in transport, thus, the positionally secure attachment in the transport container can be ensured. Thereby, even the holding device is positionable in the transport container in stable manner such that undesired falling back and forth of the holding device in the transport container can be avoided. Thereby, damage of the holding device upon transport in the transport container can also be avoided.

It can be provided that the holding device is formed in one piece. In this configuration, the support member and the holding rail are designed as a single part, however, wherein the relative mobility of these components with respect to each other is ensured. A simple and inexpensive production such as a particularly component-reduced configuration is thereby ensured. Just in a configuration of the holding device of a plastic material, thus, the manufacture, for example by an injection molding process, can be effected quickly and economically.

It can also be provided that the support member and the holding rail are separate parts. In this configuration, the individual parts can be exchanged separately taken by themselves. Thereby too, the utilization ratio can be improved.

In a preferred implementation, the support member is formed elongated and clamp-like. In particular, the support member is formed widened to the bottom. Thus, in cross-section, the support member is in particular formed as a hollow body open to the bottom, which has an inverted Y shape. In the direction of its longitudinal axis, the support member is formed linearly and formed as a hood-like receptacle for the holding rail. By this specific shaping of the support member, a particularly mechanically stable configuration can be realized, which absorbs and transfers force effects without undesired deformation upon vertically pressing down. Furthermore, thereby, the holding rail and the intraocular lens disposed thereon is surrounded in hood-like manner and protected. Not least, a particularly user-friendly and precise manageability is ensured such that the user can perform very precise and dosed movements, whereby damages to an injector or to the lens can be avoided.

Preferably, the support member has an upper narrow section and a lower wide section, and an expanding transition is formed between the sections, which in particular extends obliquely to the bottom and outwards. By this shaping, on the one hand, a particularly good gripping capability of the support member at the upper section can be allowed. Moreover, this implementation offers the secure reception and mount of the holding rail in the cavity in the upper section in specific operational states of the holding device. Further, jamming or anchoring of components of the injector, in particular cover flaps of a loading chamber, in various operational phases upon loading the lens into the loading chamber is avoidable by the shaping of the transition. A particularly smooth guiding and sliding of components along the interior side of the transition can be achieved, and a very continuous and no jerky guide of movement of the components of the injector can be achieved.

Preferably, the upper section and the transition have slits, in particular vertically oriented slits, which are formed for receiving and guiding the holding rail. Thereby, a very exact relative mobility between the support member and the holding rail can be adjusted, since virtually narrow guide tracks are preset by the slits. Undesired movements due to undesired tolerances in the guide can thereby be avoided. Furthermore, the desired movement into only one spatial direction, in particular into the vertical direction, is thereby very exactly adjustable. Further grooves are alternative embodiments instead of slits.

Preferably, guide members extend to the bottom on opposing sides of the upper section, in particular in parallel manner, and a receiving space, in particular for cover flaps of a loading chamber of an injector device, is formed between a guide member and a wall of the lower section.

Preferably, at least one bulge is formed respectively on the facing interior sides of the upper section and/or of the guide members at the transition. Thereby, a barrier or a stop for the holding rail can be provided in particularly simple, yet very effective form in various operational phases upon loading the lens into the loading chamber of the injector.

Preferably, the holding rail is movable in vertical direction relatively to the support member, and the holding rail is disposed in a starting position below the bulges upon loading the lens into the loading chamber and disposed in an end position viewed in vertical direction above the bulges, and is then held by the bulges above them.

Preferably, the holding rail has a receptacle, respectively, at a front end and at a rear end on the bottom, with which an engaging member formed in the region of a loading chamber of an injector device, respectively, engages in the assembled state. Thereby, the positional fixing between the injector device and the holding rail can be achieved securely and simply upon loading the lens into the loading chamber as well as automatically upon fitting the holding device onto the injector tube.

Furthermore, the invention relates to a packaging and transport means for an intraocular lens. The means includes a transport container and a holding device according to the invention or an advantageous development thereof. The holding device can be loaded into the transport container, and in particular, in the finished state of the packaging and transport means, the holding device is disposed in positionally stable manner in the transport container. In this final state of the packaging and transport means, an intraocular lens is disposed on the holding device. In this packaging and transport means for an intraocular lens, the already above-mentioned advantages clearly take effect. Besides an improved manageability, the damage of the intraocular lens can be reduced. Moreover, additional auxiliary tools such as for example forceps or the like are not required in order to remove the intraocular lens from the transport container upon required use in a surgical procedure.

Preferably, the intraocular lens is disposed on the holding device in a mechanically unstressed condition. Thereby too, undesired load of the intraocular lens and premature wear are avoided.

In particular, the holding device is disposed in positionally stable manner on the transport container and positioning members of the holding device are disposed non-destructively detachably in positioning regions of the transport container, particularly on the interior bottom thereof. Preferably, therefore, the holding device is fixedly positioned on the interior bottom of the transport container. Just in shipping, thus, undesired movement of the holding device in the transport container can be avoided such that undesired movement of the intraocular lens in the transport container can also be avoided. For example, a non-destructively detachable attachment can be provided in that for example a locking mechanism is formed. Thus, the positioning members can be locking members, which then engage with recesses representing positioning regions.

Therefore, the holding device can simply and unerringly be disposed and loaded in the transport container on the one hand and moreover also quickly and simply be removed from it again.

The holding device is preferably engaged closely by the container.

Preferably, a sterile liquid is contained in the transport container, in which the lens is disposed in immersed manner. After packaging and thus also in transport, the lens is surrounded by this sterile liquid such that, here too, undesired contaminations are avoided. In particular, the transport container is closed by a cover on a top side such that, here too, contaminations cannot enter the receiving space of the transport container. Moreover, in this respect, the shipping is possible without loss of liquid. Preferably, a sterile and aseptic closure of the transport container is ensured by the cover. Thus, adherence of the cover or thermally welded connection can be provided here. Therefore, the transport container is completely closed for storage and for transport. The cover can be formed transparent at least in certain regions such that the holding device and also the intraocular lens can be viewed in the transport container. Information about parameters characterizing the intraocular lens can be indicated on the cover.

Furthermore, the invention relates to an injector device for an intraocular lens, which has an injector tube, in which a plunger is displaceably disposed. Moreover, the injector device includes a loading chamber, into which the intraocular lens can be loaded. In particular, the loading chamber is formed in the injector tube. Wing-like cover flaps are disposed on the injector tube, which are movable for opening and closing the loading chamber. The injector device includes a holding device for the intraocular lens according to the invention or an advantageous development thereof. The holding device is disposed on the injector tube in the region of the loading chamber for loading the intraocular lens into the loading chamber. By this configuring injector device, a highly functional configuration can be provided, which ensures the simpler and more precise introduction of the intraocular lens into the loading chamber. In this injector device, it is particularly advantageous that if the holding device is disposed on the injector device, no further additional auxiliary tools such as forceps or the like are required in order to be able to load the intraocular lens into the loading chamber into its desired position there. The cooperation of the holding device and the injector device is matched such that the intraocular lens can automatically be loaded into the loading chamber.

The injector tube can be one piece. In a preferred embodiment the injector tube comprising two separate parts, which are assembled to each other and can be removed again in non destroying manner. Preferably a front part or front section of the injector tube comprising the loading chamber and the wing-like cover flaps an the insertion member or injection canula. This section could be assembled on the other part of the injector tube.

Moreover, it is also no longer required that the cover flaps have to be explicitly manually closed by a user by directly grasping. This is automatically ensured by the holding device.

Besides a substantially improved functional principle with regard to the introduction of the intraocular lens into the loading chamber, this can also be effected with the injector device in a more positionally stable manner and without contamination of the lens.

Preferably, for loading the intraocular lens from the holding rail into the loading chamber, the holding device is disposed on the injector tube relatively shiftable thereto. By this relative mobility of the components with respect to each other, an automatism for loading the intraocular lens into the loading chamber can be allowed.

Preferably, for loading the intraocular lens into the loading chamber, the holding device is disposed on the injector tube with its side open to the bottom and the holding rail is disposed in the loading chamber at least in partially. Undesired premature drop of the intraocular lens from the holding rail can thereby be avoided, and moreover, thus, stripping of the intraocular lens outside the loading chamber can also be avoided. For loading the intraocular lens into the loading chamber, preferably, the holding device is disposed engaging with guide tracks formed at the outside of the injector tube, along which the holding device is displaceable. The holding device is also stably positioned there in its state attached to the injector device, and undesired drop of the holding device or slipping away from the injector device can thus be avoided. Besides the mechanically stable positioning, thus, robust configuration can also be provided, which is also formed qualitatively high-grade. Undesired movement tolerances or undesired detachment of the holding device from the injector device can thereby be avoided.

Preferably, the guide tracks are formed on both sides parallel to the longitudinal axis of the injector tube. Thereby, the precise and stable guide can again be improved. Preferably, the guide tracks are disposed adjacent to an end of the loading chamber and in particular formed at the end of the loading chamber, which is turned away from the tapering insertion member of the injector device. Thus, considered in longitudinal direction of the injector device, the holding device can be fitted onto the injector tube virtually in front of the insertion member such that, here too, the positioning can be effected more stable. Since the injector tube is usually formed thicker than the insertion member, the mechanically more stable attachment can also be achieved.

Preferably, the injector device is formed such that the holding device attached to the injector device can be attacked there in a basic position, in which the guide members on the support arms of the support member of the holding device grip around the cover flaps on the upper edge, which cover flaps are disposed in an opened position. Therefore the guide members engage camlike features on the exterior surface of the flap. By the configuration, upon fitting the holding device onto the injector tube, the engagement of the guide members with the cover flaps can be ensured virtually automatically such that, here too, a simple and yet secure coupling of the components is ensured. Inconvenient additional interventions of a user are not required.

Preferably, the injector device is formed such that the cover flaps have guide tracks on the outside, with which the guide members of the support arms engage, and upon movement of the holding device from the basic position into an unloading position, the cover flaps are automatically movable into a first intermediate closure position. In particular, thus, upon the mechanic coupling between the holding device and the injector device, the guide of movement of the cover flaps is also automated, wherein this guide of movement of the cover flaps is linked to the movement of the holding device relatively to the injector device. In particular, the movement of the holding device relatively to the injector tube of the injector device is provided. Preferably, at least in certain regions, the direction of movement of the holding device relatively to the injector tube is oriented in the direction of the longitudinal axis of the injector tube. Thus, the holding device is preferably retractable with respect to the injector device, whereby the intermediate closure position of the cover flaps can be adjusted by the mechanic coupling between the guide members and the cover flaps. In particular, the guide members engage the guide tracks formed at the outsides of the cover flaps. Thereby, the movement of the cover flaps is guided in mechanically stable manner, and undesired slipping-out of the guide members from the encompassing position of the cover flaps can be avoided.

In particular, the first intermediate closure position of the cover flaps is retained by the support arms of the holding device. Here too, it is therefore not required that a user directly grasps the cover flaps in order to be able to further maintain this intermediate closure position or first to be able to adjust it fundamentally. By the mechanic coupling of the holding device and the injector device, in this respect, an automatism is generated, which ensures temporally and locally the correct movements and adjustments of the components relatively to each other, respectively. For the procedure of these different self-adjusting operations, the holding device is only to be translated into an initial movement by the user. By performing this initial movement, thus, a majority of other procedures is automatically performed.

Preferably, by the movement of the cover flaps into the first intermediate closure position, the lens disposed on the holding rail is laterally contacted by at least one interior side of a cover flap. In the first intermediate closure position, the cover flaps are closed starting from their completely opened position at least as much as they directly abut the narrow sides of the lens. Thus, mechanical retention of the lens by the cover flaps is already achieved on the one hand and the position of the lens can thus virtually no longer shift in undesired manner.

Preferably, upon a further movement of the holding device starting from this first intermediate closure position of the cover flaps, the holding rail can automatically be lifted and the lens can automatically be detached from the holding rail by this further movement of the holding device. If the support member is therefore further moved in continuation of the initial movement, thus, here too, the holding rail is automatically influenced such that it is virtually lifted upwards from the loading chamber in certain regions, thereby in turn automatically resulting in the lens being automatically detachable from the holding rail. This is in particular also achieved in that, in the previously adjusted first intermediate closure position, the cover flaps laterally abut the lens in holding manner. Here too, the further movement of the holding device is again effected at least in certain regions in longitudinal direction of the injector tube, wherein this initial movement is guided by the guide tracks in the injector tube, with which engaging members of the holding device, especially of the support member, engage.

In particular, the guide tracks are formed non-linear and are led upwards in curved manner. Thus, the movement in the direction of the longitudinal axis of the injector tube or parallel thereto is guided on the one hand, and lifting of the holding device and thus also of the holding rail into a direction perpendicular to the longitudinal axis of the tube is guided on the other hand. The entire sequence of movement of the holding device starting from the basic position of the injector device for detaching the intraocular lens from the holding device is always effected in one direction with regard to the movement in the direction of the longitudinal axis of the injector tube.

Preferably, upon a further movement of the holding device starting from that movement position, in which the lens is detached from the holding rail, the cover flap is transferred into the final closure position, wherein this is also effected automatically by the guide members upon further movement of the holding device. Thus, this is also automatically effected, without a user having to directly grasp the cover flaps in order to adjust this final closure position. Here too, it is only required to continue the initial movement of the holding device by the user in order to then be able to automatically adjust the final closure position.

Preferably, the intraocular lens is automatically folded in the loading chamber by the closure operation of the cover flaps. The folding is therefore effected in the injector tube such that, furthermore, the folded intraocular lens can be pushed from the injector tube into the tapering guide member of the injector device by the plunger.

If the cover flaps are closed and if the holding device has therefore reached its final position along the movement relative to the injector tube, thus, it can be provided that the holding device can be detachably removed from the injector tube in non-destructive manner. It can also be provided that the holding device is positionally stable disposed on the injector tube in this final position without the user having to further hold the holding device. For example, a locking position can be provided here.

It can also be provided that the above-explained positions concerning the basic position of the holding device as well as the intermediate closure positions of the cover flaps can each be felt by a user by a haptically perceivable locking position of the holding device along its initial movement path.

In a particularly advantageous implementation, the cover flaps each have plural gripping prongs at their free edges. In particular, the gripping prongs on a cover flap are disposed offset to gripping prongs on the other cover flap. By this configuration, the precise positions of the cover flaps and the holding device specific to situation can be very exactly matched to each other. Furthermore, the guide of movement as well as the mechanical contacts of the cover flaps, in particular the gripping prongs, with the holding device and the lens can be ensured extremely positionally exactly and mechanically dosed. Thereby, the touch of undesired regions is avoided. Moreover, undesired force effects on certain regions of the holding device and/or the lens by the cover flaps are also purposefully avoided.

Preferably, the holding device, in particular the support member, is movable only in one direction perpendicularly to the longitudinal axis of the injector device, in particular the injector tube, for loading the intraocular lens into the loading chamber. Thereby, the manageability of the assembly is of easy action and simple for a user. The precise movement of the components relative to each other even over small distances can thereby also be ensured and be allowed in positionally exact manner.

Preferably, for loading the intraocular lens into the loading chamber, the holding device is fitted onto the injector tube above the loading chamber. In particular, the holding rail is connected to engaging members on the injector tube and positionally fixed with the injector tube, and the support member is movable relatively thereto.

In particular, by downward moving the support member starting from a starting position after fitting the holding device onto the injector tube, the gripping prongs of the cover flaps are contacted with the interior side of the transition in a first intermediate position. The cover flaps are retained by the guide members on the holding device in axial direction.

Preferably, by further downward moving the support member, the gripping prongs are guided along the interior side of the transition oriented obliquely upwards, and thereby, the cover flaps are guided into a first intermediate closure position, in which an edge of the intraocular lens is contacted with the gripping prongs.

Starting from that, in particular by repeated further downward moving the support member, the intraocular lens is automatically removed from the holding rail and is automatically folded and is loaded into the loading chamber, and the cover flaps are automatically brought into a closure position.

In a further embodiment there are no gripping prongs on the cover flaps and the inner sides of the cover flaps are formed in such a way, that the automatic engaging of the lens is possible as well, whereas the steps from the open position to the complete closed position of the flaps are comparable with the steps done by the embodiment with these gripping prongs. The difference to the embodiment with the gripping prongs is in contacting the lens only with the specially formed inner sides of the flaps.

Furthermore, the invention relates to a method for packaging an intraocular lens, in which the lens is attached to a holding device according to the invention or an advantageous development thereof. The holding device is loaded into a transport container in positionally fixed manner such that the lens is positioned in the transport container in a sterile liquid in immerged manner. The lens can be sterilized by steam sterilization. Preferably, moreover, it is provided that the injector device is sterilized by ETO methods at least in certain regions, in particular on its interior side of the injector tube and of the insertion member.

Advantageous implementations of the holding device according to the invention as well as the advantageous implementations of the packaging and transport means and the advantageous implementations of the injector device are to be considered as advantageous implementations of this method with regard to the packaging of the intraocular lens in the transport container.

Furthermore, the invention relates to a method for loading an intraocular lens into an injector device, wherein the injector device is formed according to the injector device according to the invention or an advantageous development thereof. The intraocular lens is automatically loaded from the holding device into a loading chamber of the injector device by the cooperation between the holding device and the injector tube having cover flaps for closing the loading chamber. The mechanic coupling between the holding device and the injector device as well as the relative mobility between the holding device and the injector tube allows the automatic introduction of the intraocular lens into the loading chamber with automatic movement of the cover flaps from the opened position into the completely closed position at the same time. These approaches are performed without gripping the lens with further auxiliary means or auxiliary tools such as forceps or the like, and moreover, the user also does not have to directly grasp the cover flaps any longer in order to be able to actuate them. In the method for loading the intraocular lens into the loading chamber of the injector device, with fitted holding device on the injector device, the user only takes action to that effect that he grasps the holding device on a gripping member of the support member and actuates the holding device relatively to the injector tube along an initial path. Due to the mechanic coupling of the holding device to the injector device, all of the further operations concerning the removal of the lens from the holding device and the loading of the lens into the loading chamber as well as the closure of the cover flaps are automatically performed. By the mechanic coupling between the holding device and the injector device, in particular of special components of the respective devices, these procedures for loading the intraocular lens are performed both temporally and locally in matched order depending on the initial movement of the holding device in precisely and self-initiating manner. Undesired positions of the intraocular lens and of the cover flaps can therefore be avoided at any time during the loading operation.

Advantageous developments of the holding device and of the injector device are to be considered as advantageous developments of the method for loading an intraocular lens into an injector device.

As a whole, by the holding device, the packaging and transport means and the injector device, an overall system is provided, which ensures a highly functional procedure from the manufacture and packaging of the lens up to the insertion of the lens into the eye. In particular, this is improved with regard to the satisfaction of the sterilization operations and the aseptic treatment of the lens and with regard to user-friendly manageability and matched procedures upon the use of the lens. If virtually such a lens is used in a surgical procedure and if the packaging and transport means of the intraocular lens according to the invention or an advantageous development thereof is already delivered to the medical personnel, thus, there only has to be opened the package by removing the cover from the transport container. The medical personnel just has to remove the holding device from the transport container by gripping the gripping member and fit it onto the injector device and perform the explained initial movements in order to be able to achieve the further automatic loading of the injector tube with the lens.

Further features of the invention appear from the claims, the figures and the description of figures. The features and feature combinations mentioned above in the description as well as the features and feature combinations mentioned below in the description of figures and/or shown in the figures alone are usable not only in the respectively indicated combination, but also in other combinations or alone without departing from the scope of the invention. In particular, therefore, single features or feature combinations of an embodiment can be combined with features and feature combinations of another embodiment in order to be able to generate new embodiments.

BRIEF DESCRIPTION OF THE DRAWINGS

Embodiments of the invention are explained in more detail below based on schematic drawings. There show.

PREFERRED EMBODIMENTS OF THE INVENTION

Figure 1:
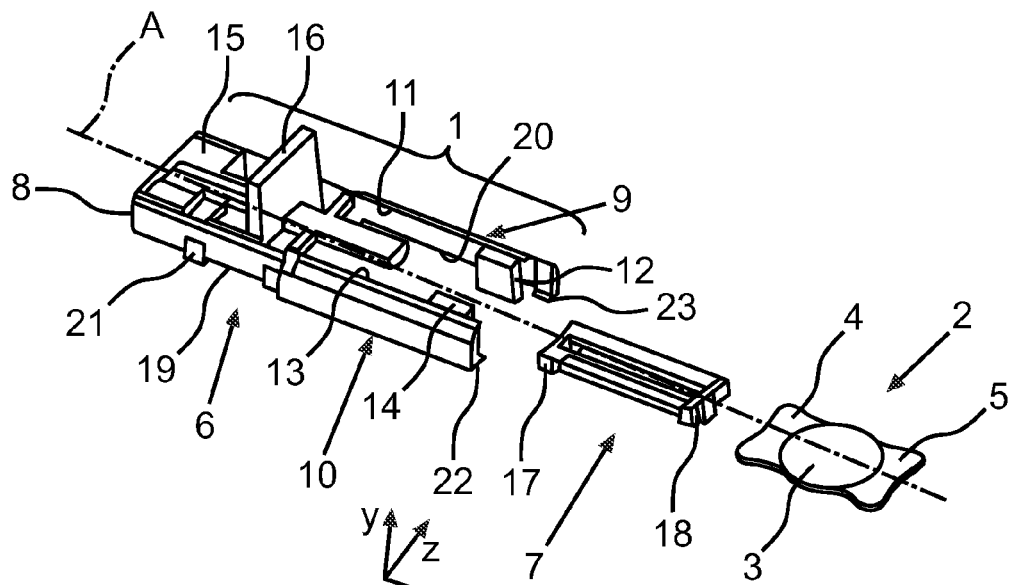
FIG. 1 a perspective exploded representation of an embodiment of a holding device according to the invention.

In the figures, functionally similar elements are provided with the same reference characters.

The present invention is applicable in surgical procedures on the eye, in which a very small incision for introducing the intraocular lens is provided, which is for example performed in so-called MICS (Micro Incision Cataract Surgery) methods. However, utilization is also possible, in which these minimal incisions on the eye are not performed and greater incisions for introducing the intraocular lens are provided.

The invention consists of a comprehensive system that includes both a storage device for the intraocular lens (IOL) and an injector into which the IOL is transferred with minimum manual manipulation, prior to delivery. Notably, the solution addresses both of the factors described above that have prevented success in MICS techniques with simple-to-use systems:

The system packages the IOL (which is preferably steam sterilized) separate from the lumen (which is preferably ETO sterilized). This separation of the lumen of the IOL avoids the need to expose the lumen to the steam sterilization process. Steam sterilization compromises even the optimal material/coating technologies. Thus, this separation is a central for optimal lubricity of the lumen at the time of end use.

The system folds and compresses the IOL. Therefore, its stability to achieve MICS incision targets is at least equivalent to conventional cartridge-handpiece systems. Indeed, the proposed invention is differentiated from a conventional cartridge-handpiece system primarily through the means of loading the IOL into the system. Therefore, the invention essentially mechanizes what is previously a purely manual process.

It is also notable such a system could also be employed in non-MICS devices, were these of use would itself be a benefit over existing systems. This could also include hydrophilic versions where the IOL-containing storage device would be preinstalled onto the injector; requiring only movement of this device in order to load the lens into the injector for delivery.

In FIG. 1, in a perspective exploded representation, a holding device 1 for an intraocular lens 2 is shown. In the embodiment, the intraocular lens 2 is formed such that it has an optic part 3 and two haptic parts 4 and 5 disposed on opposing sides of the optic part 3. The holding device 1 is formed for holding the intraocular lens 2, wherein the configuration of the intraocular lens 2 is only exemplary. Other configurations of intraocular lenses can also be held by the holding device 1. The holding device 1 includes a support member 6 formed in one piece. Moreover, the holding device 1 includes an elongated holding rail 7, which is disposed movably on the elongated support member 6. The support member 6 and the holding rail 7 can be formed both as separate components and integrally with each other.

On the bottom and thus upon viewing in positive y-direction, the support member 6 is formed open from below. In corresponding manner, this applies to the holding rail 7. The holding rail 7 is moreover also formed laterally open upon viewing in positive and negative z-direction.

The support member 6 has a base body 8. On the base body 8, a first support arm 9 and a second support arm 10 are attached to the front side of the base body 8. The support arms 9 and 10 are disposed and formed on both sides of the longitudinal axis A of the support member 6 and in particular symmetrically thereto. The support arms 9 and 10 therefore also extend parallel to the axis A.

On an interior side 11 of the support arm 9, a guide member 12 is disposed. In analog manner, on an interior side 13 of the support arm 10, there is also disposed a guide member 14. Between the interior side 11 and the guide member 12, an engagement space is disposed, wherein it is formed in analog manner between the interior side 13 and the guide member 14. The guide members 12 and 14 are disposed on the same level with regard to the view in the direction of the axis A in x-direction.

On an upper side 15 of the base body 8, a gripping member 16 is formed. On this gripping member 16, a user can grasp the holding device 1 and correspondingly lift or actuate it.

The elongated holding rail 7 is disposed movably on the support member 6. Therein, the mobility is possible in the direction of the longitudinal axis A and in the direction perpendicular thereto along an axis extending in y-direction.

The holding rail 7 has gripping members 17 and 18 disposed on the bottom side on its opposing ends, which are provided for gripping the intraocular lens 2 and thus for holding the intraocular lens 2. The gripping members 17 and 18 grip the haptic parts 4 and 5 of the intraocular lens 2.

If the intraocular lens 2 is disposed on the holding device 1, thus, it is freely accessible from the bottom.

Moreover, positioning members 21, 22 and 23 are formed on the support member 6 on a lower border 19 and 20 preferably both on the base body 8 and on the support arms 9 and 10. These positioning members can for example be provided as flexibly movable locking tabs. Therefore, the holding device 1 can be disposed positionally fixed for example in a packaging and transport means.

The held intraocular lens 2 is completely and freely accessible from the bottom through the support member 6, since the holding device 1 has no cover on the bottom. However, moreover, the intraocular lens 2 is protected from the top and laterally since the support member 6 virtually forms a cavity, in which the holding rail 7 and the intraocular lens 2 are received. In simplified view, the support member 6 is formed as an inverted U shape in cross-section. In particular, this applies in the region of the base body 8.

Figure 2:
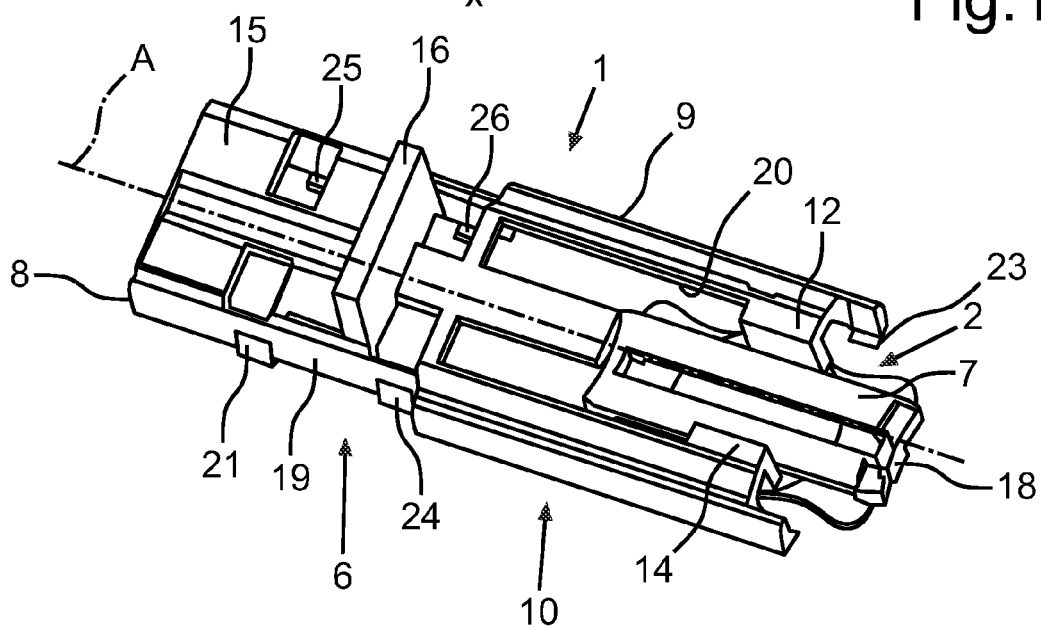
FIG. 2 a perspective representation of the holding device according to FIG. 1 in the assembled state.

In FIG. 2, a perspective inclined top view of the holding device 1 in the assembled state with held intraocular lens 2 is shown. The intraocular lens 2 is disposed below the guide members 12 and 14 and the holding rail 7 is held in the support member 6. Moreover, further positioning members 24, 25 and 26 disposed symmetrically to the axis A are shown, which are formed on the base body 8 on the lower border 19.

Figure 3:
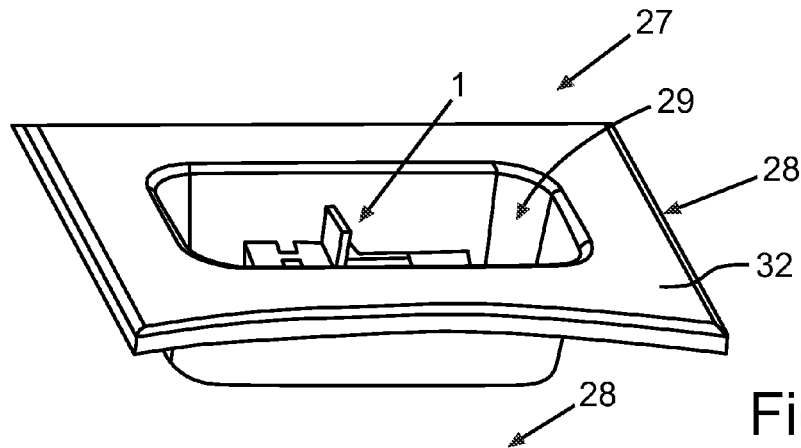
FIG. 3 a perspective representation of an embodiment of a packaging and transport means according to the invention.

In FIG. 3, in a perspective representation, a packaging and transport means 27 for an intraocular lens 2 is shown. The means 27 includes the holding device 1 according to the representations in FIGS. 1 and 2. This holding device 1 is disposed in a transport container 28. Thereto, the transport container 28 includes a receiving space 29, in which the holding device 1 is positionally fixedly disposed. Thereto it is provided that the positioning members 21 to 26 are disposed engaging with corresponding positioning regions in an interior bottom 30 (FIG. 4) of the transport container 28. Therefore, the holding device 1 cannot slip or displace by itself from the illustrated position even upon movement or inversion of the transport container 28.

With regard to the positioning, on this interior bottom 30, an elevation 31 is formed, in which the positioning regions are formed. The intraocular lens 2 is attached to the holding device 1 in mechanically unstressed manner.

The receiving space 29 is filled with a sterile liquid such that the intraocular lens 2 is immersed in this liquid. Moreover, the means 27 includes a cover not illustrated in FIG. 3, which is attached to the top 32 of the transport container 28 and protects the receiving space 29 from escape of liquid. An intraocular lens 2 packaged in this manner can then be shipped and arrives accordingly at the required location, for example at an ophthalmologist, in this respect.

Figure 4:
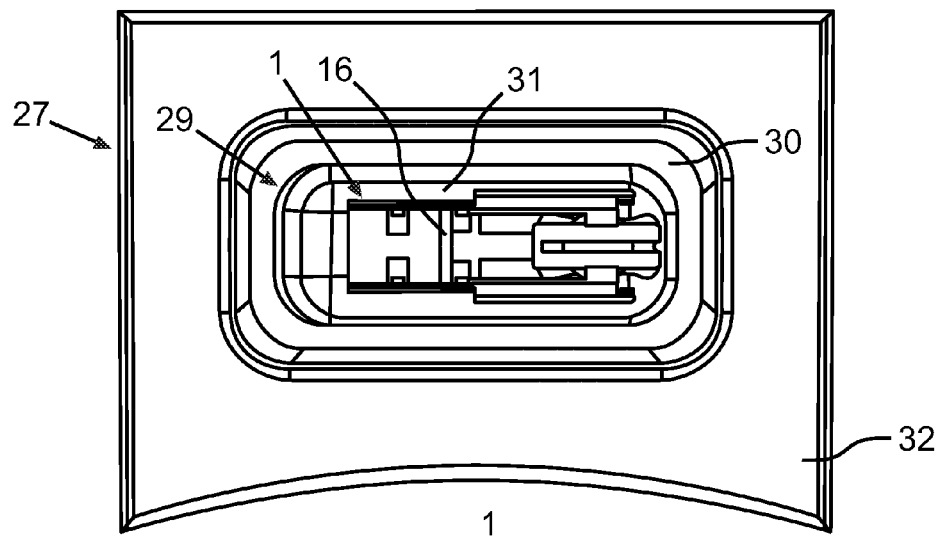
FIG. 4 a top view of the packaging and transport means according to FIG. 3.

In FIG. 4, a top view of the means 27 and the transport container 28 is shown. The holding device 1 is disposed in the receiving space 29 such that, after removing the cover, the holding device 1 can simply be gripped on the gripping member 16 and can be withdrawn from the fixed position.

Figure 5:
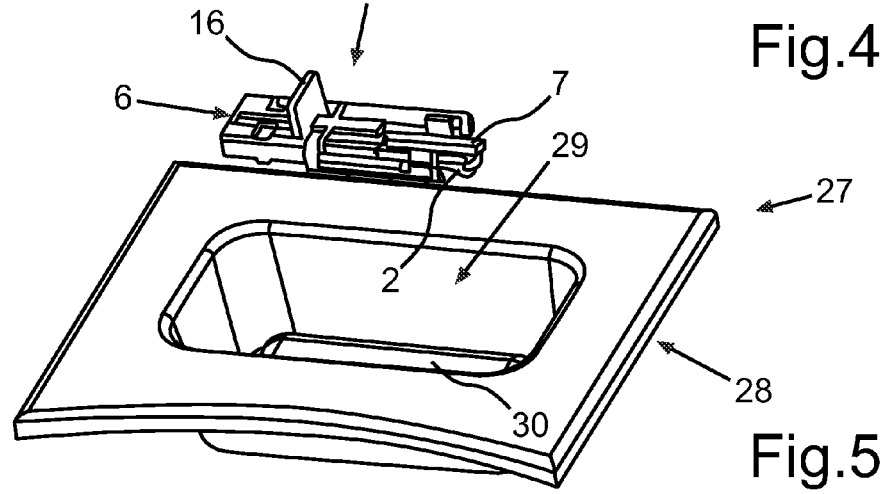
FIG. 5 a further perspective representation of the packaging and transport means according to FIGS. 3 and 4 with already removed holding device.

In FIG. 5, with respect to that, the removed position of the holding device 1 from the transport container 28 is shown.

Figure 6:
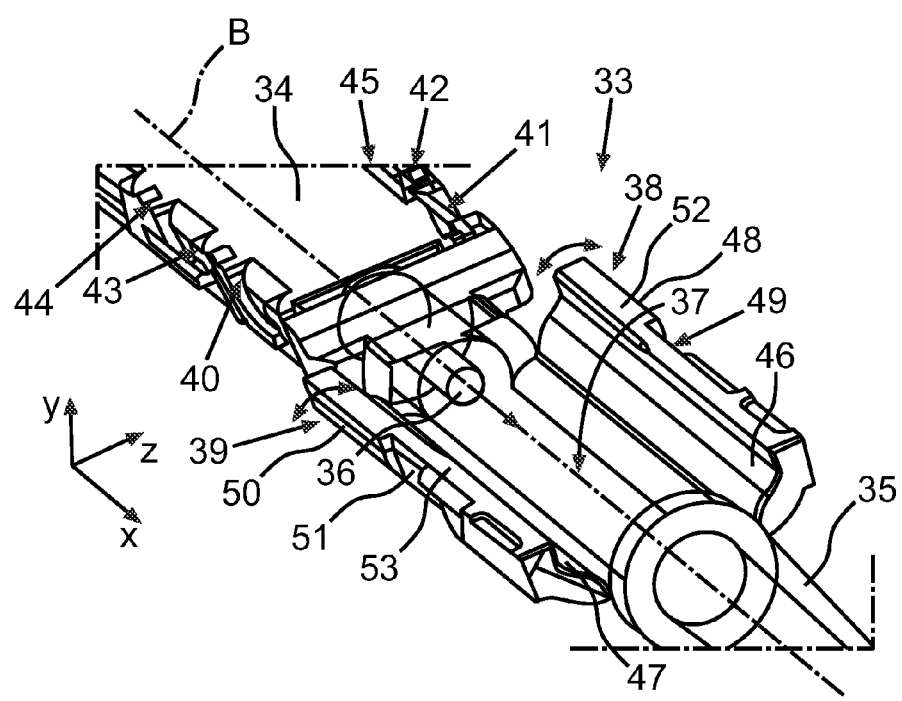
FIG. 6 a perspective representation of a section of an embodiment of an injector device according to the invention.

In FIG. 6, in a perspective representation, a partial section of an embodiment of an injector device 33 according to the invention is shown. The injector device 33 includes an injector tube 34, to the front side of which a tapering hollow insertion member 35 joins. This insertion member 35 is provided for introducing through the incision in the eye for inserting the intraocular lens 2 into the eye.

The injector tube 34 is also formed hollow and a plunger 36 is movable in the injector tube 34 along the longitudinal axis B of the injector tube 34. The intraocular lens 2 is pushed out of the injector device 33 through the insertion member 35 by the plunger 36. The injector device 33 has a loading chamber 37 in the interior of the injector tube 34. The loading chamber 37 is closable by wing-like formed cover flaps 38 and 39. In the representation according to FIG. 6, these cover flaps 38 and 39 are shown in the completely opened position. They can be pivoted in the corresponding directions according to the shown double arrows. By means of the cover flaps 38 and 39, the loading chamber 37 can be closed. The cover flaps 38 and 39 are disposed on the injector tube 34 by means of hinges such that they can be pivoted correspondingly.

At an outside, curved guide tracks 40 and 41 are formed on opposing sides of the axis B on the injector tube 34. Moreover, further engagement regions 42, 43, 44 and 45 are provided. By means of these guide tracks 40 and 41 and the engagement regions 42 to 45, the holding device 1 can be attached to the injector device 33 and in particular to the injector tube 34 and be moved relatively with respect to the injector tube 34. By the engagement with the guide tracks 40 and 41 and optionally with the engagement regions 42 to 45, the holding device 1 can also be moved relatively to the injector tube 34 without the holding device 1 dropping from the injector tube 34.

In particular, the support member 6 engages these guide tracks 40 and 41 and depending on the displacement position also one or more engagement regions(s) 42 to 45.

An interior side 46 is formed on the cover flap 38, which is formed unevenly in direction of revolution around the axis B. In corresponding configuration, an interior side 47 is formed on the cover flap 39.

Moreover, a guide track 49 is formed at an outside 48 of the cover flap 38. In corresponding manner, a corresponding guide track 51 is formed at an outside 50 of the cover flap 39. The cover flap 38 has a free edge or border 52, wherein the cover flap 39 has a free edge or border 53. In the closed state of the cover flaps 38 and 39, preferably, these two edges 52 and 53 are disposed abutting each other.

Figure 7:
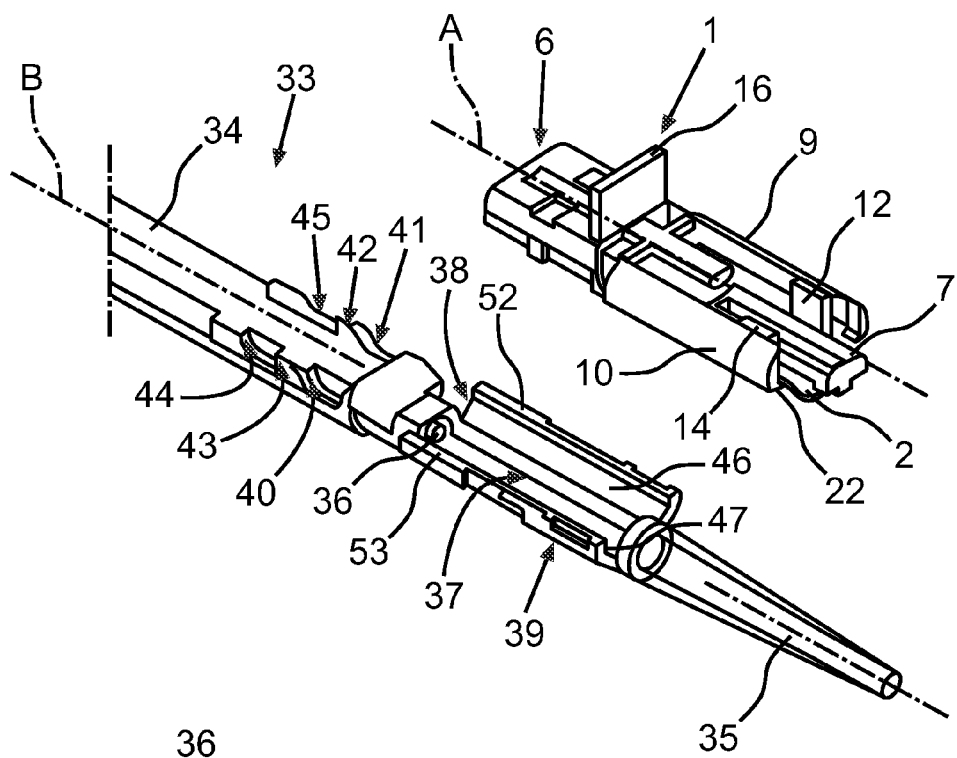
FIG. 7 a perspective representation of the injector device according to FIG. 6 with a holding device separated from it according to FIGS. 1 and 2.

In FIG. 7, in a further perspective representation, the injector device 33 according to the representation in FIG. 6 is shown, wherein the holding device 1 still separated from it with the intraocular lens 2 is additionally shown.

After the holding device 1 has been removed from the means 27 according to the representation in FIG. 5, afterwards, it is fitted onto the injector device 33. Based on the representation in FIG. 7, for this, the support member 6 is preferably inserted into the guide tracks 40 and 41 on the injector tube 34 with appropriate corresponding engagement members. Optionally, in addition to that, an engagement of members of the support member 6 with one or more of the engagement regions 42 to 45 can also be provided.

Figure 8:
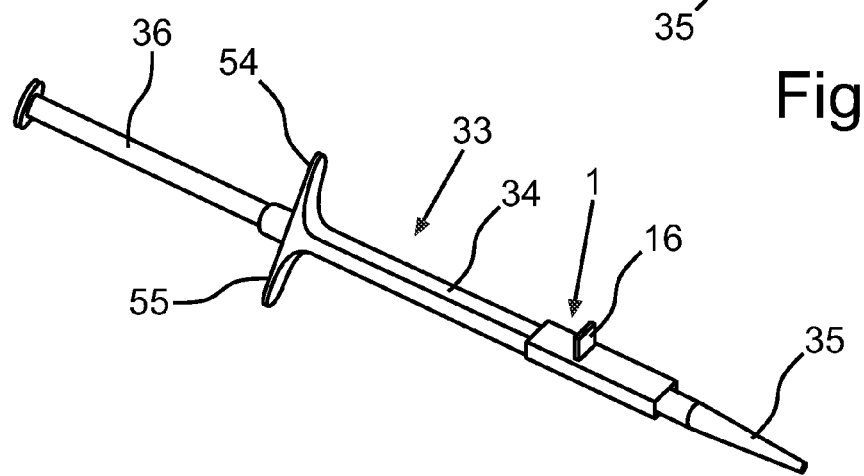
FIG. 8 a perspective representation of the injector device with fitted holding device.

In FIG. 8, in a perspective representation, the entire injector device 33 with the fitted holding device 1 is shown. Therein, the holding device 1 is positioned on the top of the injector tube 34 and the holding rail 7 is disposed within the loading chamber 37 at least in certain regions. Thereby, the intraocular lens 2 cannot drop from the holding rail 7 in undesired manner and for example cannot fall onto the floor outside of the loading chamber 37.

Viewed in the direction of the axis B, the guide tracks 40 and 41 as well as the engagement regions 42 to 45 are formed adjacent to the loading chamber 37 at the outside of the injector tube 34. In the fitted state of the holding device 1, the longitudinal axis A thereof extends parallel to the axis B.

After the mechanic coupling to the injector device 33, the holding device 1 is movable along the guide tracks 40 and 41 and therefore, movements along the longitudinal axis B as well as upwards or downwards thereto can be performed.

In FIG. 8, a basic position of the holding device 1 is shown, in which it is disposed on the injector device 33. Upon fitting the holding device 1 onto the injector device 33, it is automatically achieved that the guide members 12 and 14 on the support arms 9 and 10 grip around the cover flaps 38 and 39 on the upper free edges 52 and 53 thereof. Moreover, it can be provided already in this basic position that members of the holding device 1 in particular formed on the support arms 9 and 10 engage the guide tracks 49 and 51 of the cover flaps 38 and 39. It can also be provided that such engagement is only effected upon further movement of the holding device 1 relative to the injector tube 34.

According to the representation in FIG. 8, holding grips 54 and 55 are attached to the injector tube 34, which can be gripped to be able to ensure a counter-pressure upon displacement of the plunger 4.

Figure 9:
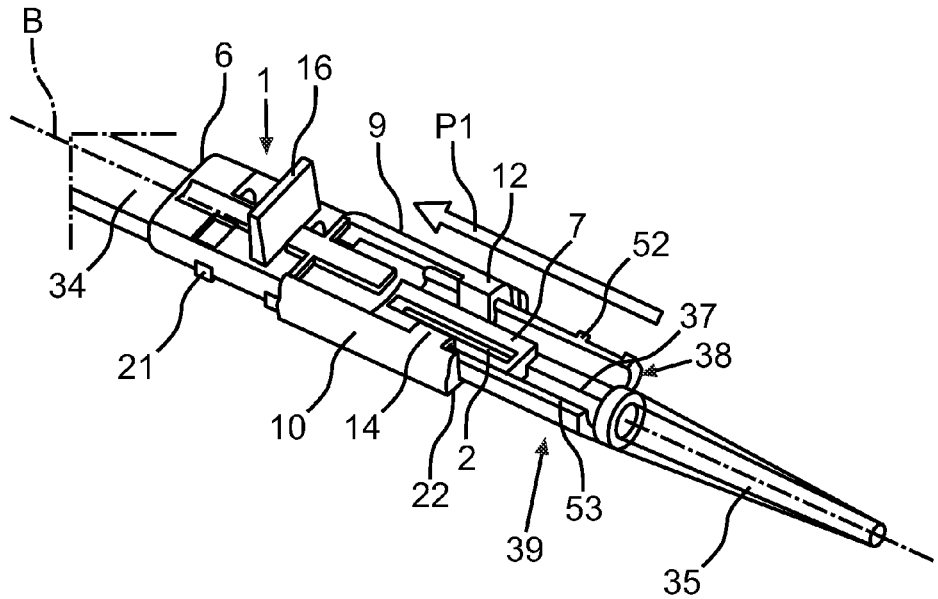
FIG. 9 a perspective representation of the injector device with the holding device in a specific operational state upon insertion of the intraocular lens into the loading chamber of the injector device.

In FIG. 9, a further perspective representation of a partial section of the injector device 33 with the holding device 1 is shown. Starting from the basic position of the holding device 1 on the injector tube 34 shown in FIG. 8, in FIG. 9, a displacement from the basic position is shown. For introducing the intraocular lens 2 into the loading chamber 37, the holding device 1 is pulled upwards according to the arrow representation P1 in the direction of the axis B. This movement is guided by the guide tracks 40 and 41. In particular, a user grips the gripping member 16 on the holding device 1 and pulls it back or upwards, respectively, according to the arrow representation P1 in the direction of the axis B. By this movement from the basic position, it is achieved that the cover flaps 38 and 39 are automatically folded from the completely opened position into a first intermediate closure position on the one hand. Then, it is automatically held by the holding device 1, in particular by the support arms 9 and 10 and the guide members 12 and 14 disposed thereon. The path of movement starting from the basic position into the first displacement position of the holding device 1 shown in FIG. 9 is for example a few millimeters, in particular about 2 mm. By this translation of the cover flaps 38 and 39 into this first intermediate closure position, moreover, it is automatically also achieved that the interior sides 46 and 47 of the cover flaps 38 and 39 abut the exterior free accessible edge sides of the intraocular lens 2 and directly contact it. Thereby, the intraocular lens 2 is held by the cover flaps 38 and 39 in some manner.

Starting from the first displacement position of the holding device 1 according to the representation in FIG. 9, then, a further movement of the holding device 1 by further retraction is performed. Furthermore, this is shown in the representation according to FIG. 10. By this further movement starting form the reached first displacement position of the holding device 1, the holding rail 7 is automatically pushed upwards out of the loading chamber 37 and the intraocular lens is automatically detached from the holding rail 7.

Figure 10:
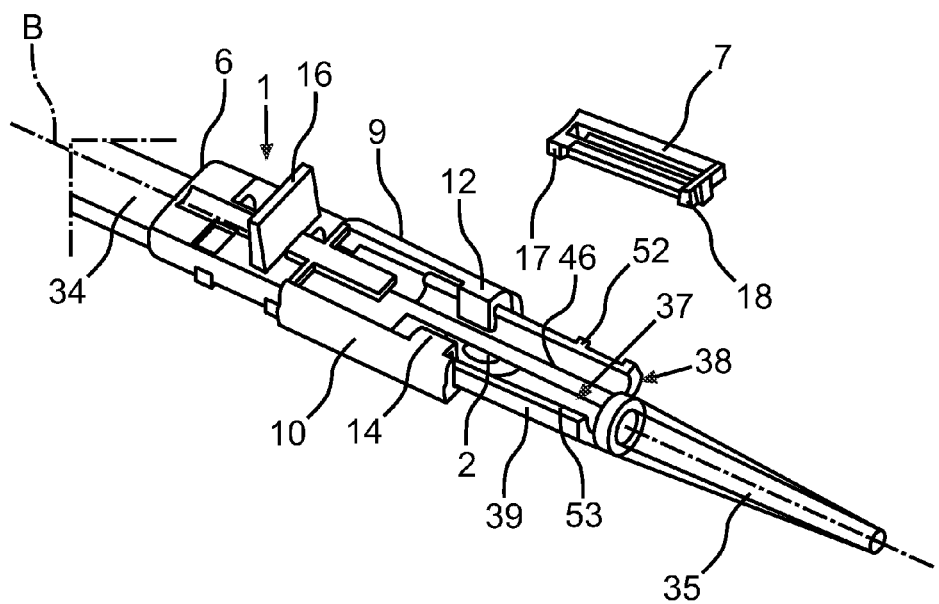
FIG. 10 a further perspective representation of the injector device with the holding device in a second operational state upon insertion of the intraocular lens.

In FIG. 10, a state is here already shown, in which the holding rail 7 is completely removed from the loading chamber 37 and is removed from the support member 6. This is only an exemplary configuration and it can also be provided that the holding rail 7 further remains disposed on the support member 6. In this second displacement position of the holding device 1 shown in FIG. 10, moreover, a second intermediate closure position of the cover flaps 38 and 39 is also reached. Based on the representation in FIG. 9, namely, upon further retraction of the holding device 1 in the guide of movement, it is achieved that the cover flaps 38 and 39 are further closed by the support arms 9 and 10 and the guide members 12 and 14. Thereby, rolling-up or folding of the intraocular lens 2, respectively, is also already allowed.

Figure 11:
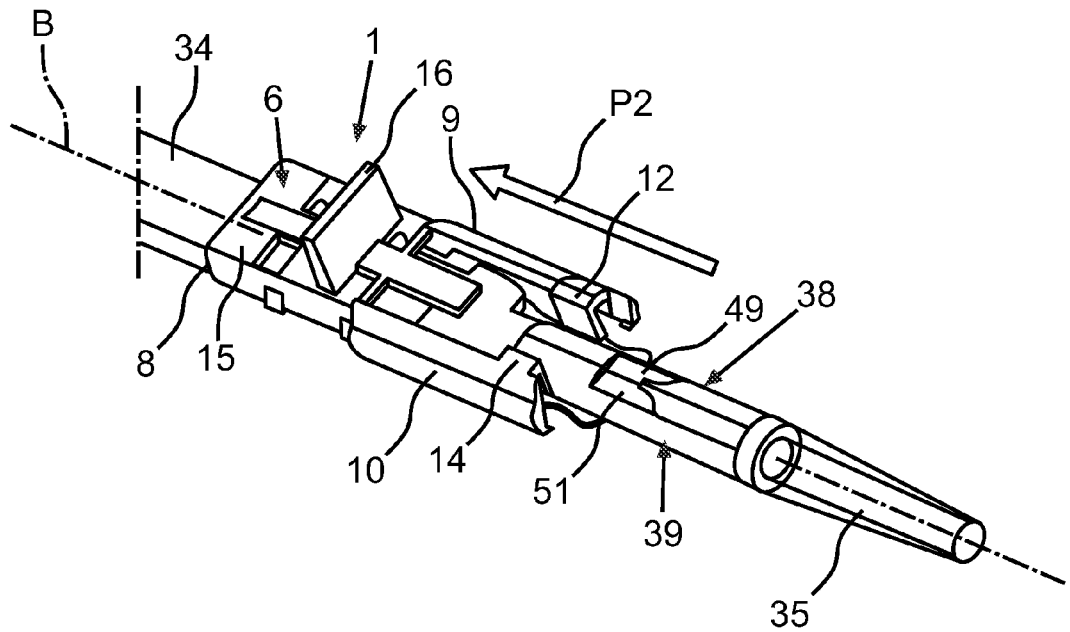
FIG. 11 a further perspective representation of the injector device with the holding device in a third operational state upon insertion of the intraocular lens.

Starting from this reached second displacement position of the holding device 1 and the second intermediate closure position of the cover flaps 38 and 39, then, on the further initial path of the holding device 1, it can be even further retracted. This is effected according to the arrow representation P2. By this further advancement, automatic complete closure of the cover flaps 38 and 39 is effected by the support arms 9 and 10 and the guide members 12 and 14, as it is shown in the representation of FIG. 11. Thereby, the intraocular lens 2 contained in the loading chamber 37 is also automatically further rolled up.

Starting from this reached complete closure position of the cover flaps 38 and 39 and the reached further displacement position of the holding device 1 on the injector tube 34, it is then possible that the holding device 1 afterwards remains on the injector tube 34. For this, it can be provided that a further displacement is effected and engagement of the support member 6 with engagement regions 42 to 45 is effected or a further other position is occupied therein upon already effected engagement with these engagement regions 42 to 45. The holding device 1 is then held positionally stable on the injector tube 34.

It can also be provided that a further movement of the holding device 1 by actuation by a user is performed starting from the representation in FIG. 11, and thereby the holding device 1 automatically detaches itself from the injector tube 34 due to the guide tracks 40 and 41 and optionally to the engagement regions 42 to 45.

Figure 12:
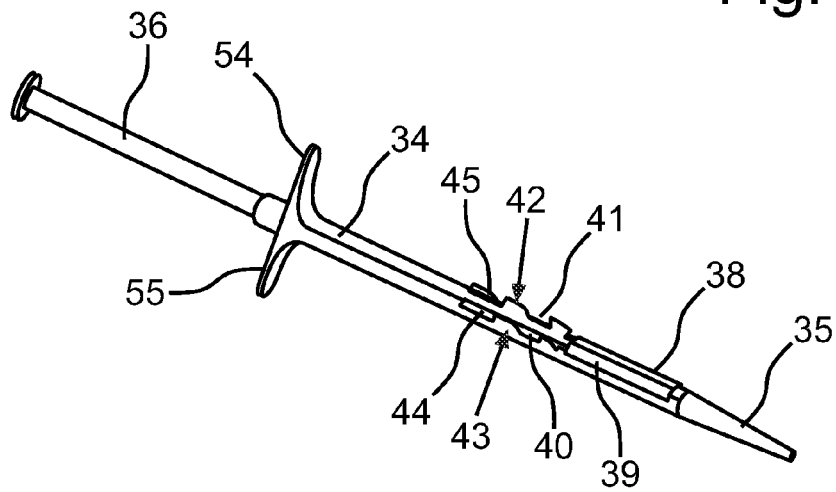
FIG. 12 a further perspective representation of the injector device with intraocular lens inserted in the loading chamber and removed holding device.
Figure 13:
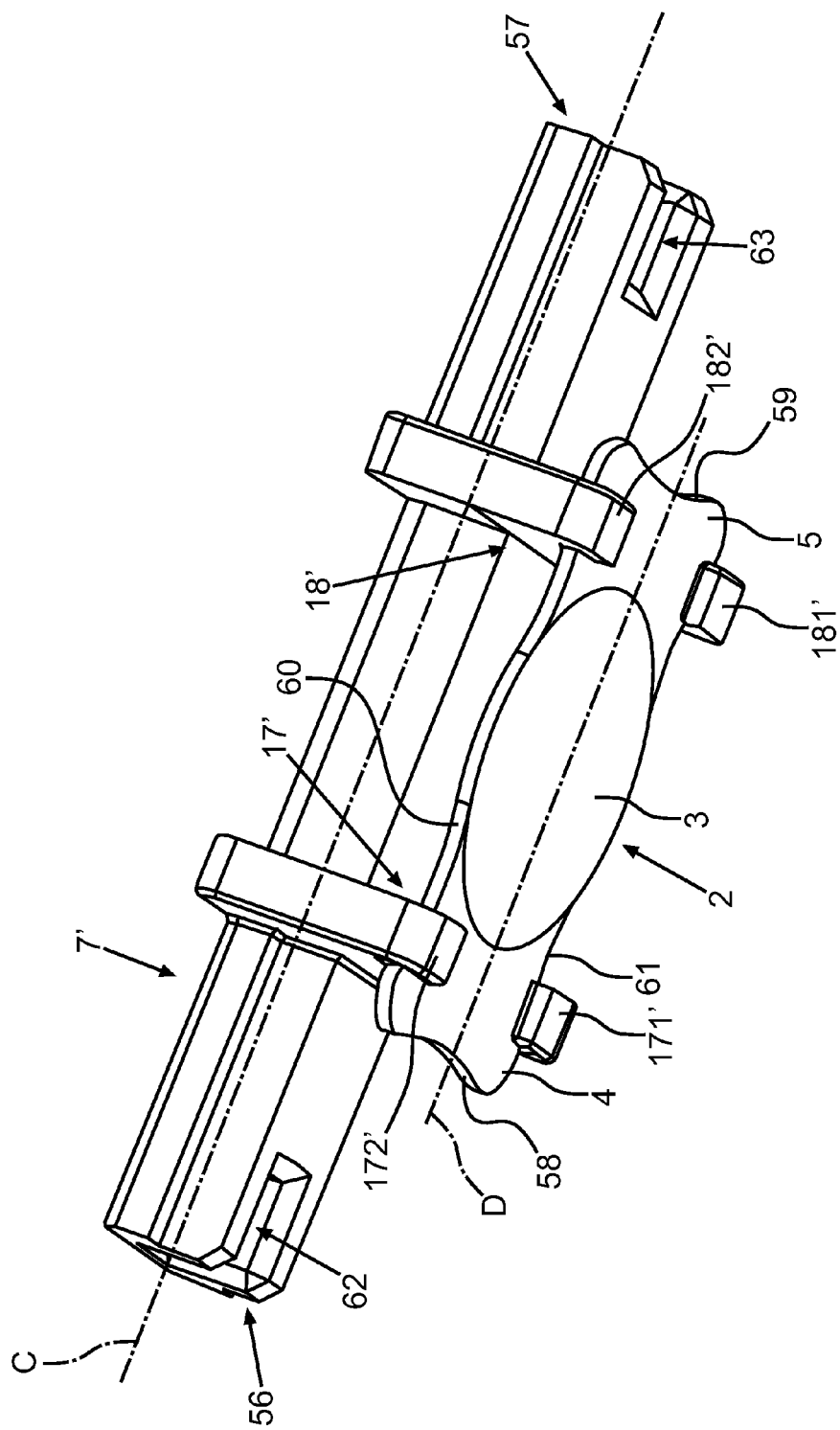
FIG. 13 a perspective representation of a further embodiment of a holding rail of a holding device.

For example, this is shown in the perspective representation in FIG. 12, in which the injector device 33 is loaded with the intraocular lens 2 in the loading chamber 37, the cover flaps 38 and 39 are completely closed and the holding device 1 is separated from the injector device 33.

If the holding device 1 remains disposed on the injector tube 34 based on the representation in FIG. 11, thus, furthermore, this can also be used in that the cover flaps 38 and 39 are in contact with the support arms 9 and 10 and/or the guide members 12 and 14 and thereby the cover flaps 38 and 39 are kept closed.

Thus, the intraocular lens 2 is already completely rolled up or folded in the loading chamber 37 such that this state is already formed before introduction into the insertion member 7.

During the entire process starting from the attached state of the intraocular lens 2 to the holding rail 7, in the further process of packaging, of the attachment of the holding device 1 to the injector device 33 and of the insertion of the intraocular lens 2 into the loading chamber 37 up to the insertion of the intraocular lens 2 then into the eye with the injector device 33, the intraocular lens 2 is no longer directly contacted by the user or even no longer by an additional auxiliary tool such as for example forceps or the like. Moreover, for the entire process from the removal of the holding device 1 from the means 27 up to the complete insertion of the intraocular lens 2 into the loading chamber 37 with closed cover flaps 38 and 39, it is no longer required that except for the contact with the gripping member 16 of the holding device 1 and the holding of the injector tube 34, further components, in particular the cover flaps 38 and 39, have to be directly contacted and actuated.

It can be provided that on the initial path of the actuation of the holding device 1, the basic position and the further displacement positions as well as the intermediate closure positions of the cover flaps 38 and 39 associated therewith as well as the final position are haptically perceivable for a user. For example, this can be each formed by gentle slide into a smooth locking position. By the mechanic coupling of the holding device 1 to the injector tube 34 by the guide tracks 40 and 41 and optionally the engagement regions 42 to 45 and corresponding members on the holding device 1, undesired movement of the holding device 1 relative to the injector tube 34 can also be avoided. Moreover, the desired relative mobility of these components is securely and precisely permitted at the same time.

Preferably, the cover flaps 38 and 39 are formed such that they remain self-retaining in the completely closed position shown in FIGS. 11 and 12.

It can also be provided that the initial path or the movement path of the holding device 1, respectively, according to the explanations to FIGS. 8 to 12 occurs in reverse direction according to the explained initial path and the movement is performed in the direction of the insertion member 7.

Moreover, the system is formed such that different configurations of plungers can be used. Moreover, a plurality of different intraocular lenses can be held with the holding device 1 and be loaded into the loading chamber 37. The intraocular lenses can be formed differently with regard to their configuration and number of haptic parts. They can be formed as one-piece or multi-piece lenses.

In the further FIGS. 13 to 22, a preferred embodiment is shown. In this implementation, a holding device 1' (FIG. 14) includes a holding rail 7' shown in FIG. 13 in perspective representation. In this embodiment, in distinction from the configuration according to FIGS. 1 to 12, the holding rail 7' includes gripping members 17' and 18', but which are not disposed at the ends 56 and 57 opposing viewed in longitudinal direction C, but are offset with respect to that. The gripping member 17' has two gripping hooks 171' and 172'. In corresponding manner, the gripping member 18' has gripping hooks 181' and 182'. In distinction from the configuration according to FIGS. 1 to 12, the gripping members 17' and 18' do not grip the front edges 58 and 59 of the haptic parts 4 and 5 viewed in longitudinal direction D of the lens 2, but lateral edges 60 and 61 of these haptic parts 4 and 5.

Moreover, in the region of the ends 56 and 57 of the holding rail 7', a receptacle 62 and 63 is formed, respectively. In the embodiment, these receptacles 62 and 63 are formed open on the front sides of the ends 56 and 57. With respect to that, a closed configuration can also be provided. Engaging members disposed on the injector tube adjacent to the loading chamber engage with these receptacles 62 and 63 in the assembled state of the holding device 1'. Thereby, the positionally fixed arrangement of the holding rail 7' with the injector tube is then given.

As can be appreciated, this holding rail 7' is also formed open to the bottom, and the lens 2 is freely accessible both from below and from the sides.

Figure 14:
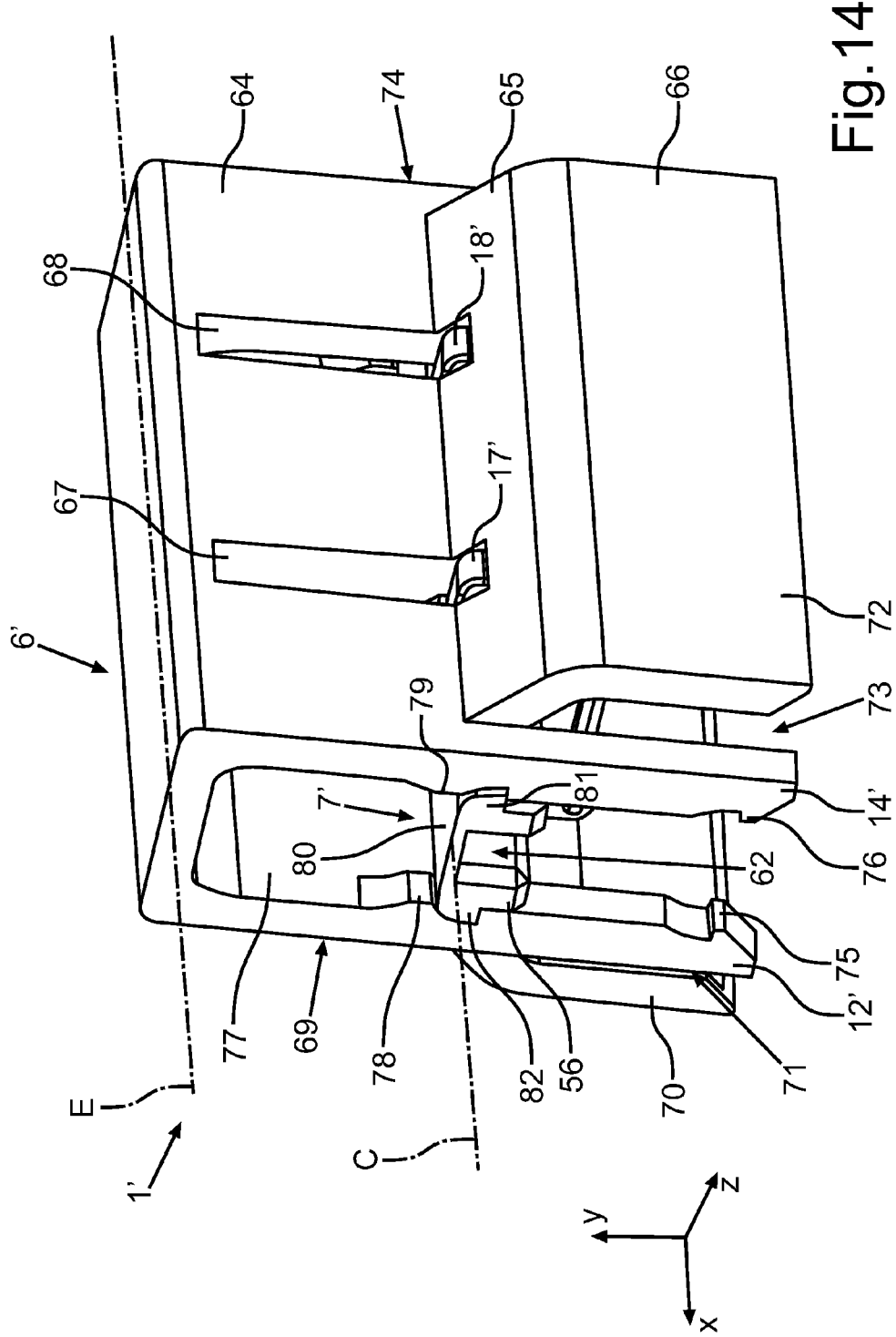
FIG. 14 a perspective representation of a further embodiment of a holding device.

In FIG. 14, a preferred embodiment of a holding device 1' is shown in perspective representation. This holding device 1' includes a support member 6' besides the holding rail 7' shown in FIG. 13. The support member 6' is formed elongated and designed clamp-like. In the first approximation, the support member 6' can be considered as an inverted Y shape in cross-section. The support member 6' has a longitudinal axis E and is also formed open to the bottom. The clamp-like structure formed open to the bottom results from the support member 6' having an upper section 64, to which a transition 65 adjoins. At this transition 65, a second lower section 66 forms adjoining, which is wider with respect to the narrower upper section 64. The transition 65 is oriented obliquely outwards.

Thus, the support member 6' presents a hollow rail open to the bottom.

In the upper section 64, slits 67 and 68 oriented vertically and thus perpendicularly to the longitudinal axis E are formed, which are also formed in pairs on the opposing side. The slits 67 and 68 as well as the opposing corresponding slits are continuous and provided for guiding the holding rail 7' upon a vertical movement in y-direction relative to the support member 6'. It can be appreciated that in the basic position or starting position of the holding rail 7', respectively, shown in FIG. 14 within the cavity of the support member 6', the gripping members 17' and 18' extend into these slits 67 and 68.

By this configuration, merely such a vertical movement of the holding rail 7' relative to the support member 6' is possible.

Adjoining to the upper section 64, at a front end 69 of the support member 6', guide members 12' and 14' extend downwards. Viewed in z-direction, the guide members 12' and 14' are positioned such that the walls of the lower section 66 are each located further outwards such that a receiving space 71 is formed between a guide member 12' and the adjacent wall 70 of the lower section 66. A cover flap for closing the loading chamber can extend into it in the state of the holding device 1' fitted onto the injector tube. In corresponding manner, a free space or a receiving space 73, respectively, is also designed between the opposing guide member 14' and an opposing wall 72 of the lower section 66, with which the opposing cover flap can engage correspondingly. In corresponding manner, at a rear end 74 of the support member 6', corresponding further guide members not recognizable are formed. The guide members 12' and 14' have hook-like holding members 75 or 76, respectively, which are formed for holding and for engaging with a section of an injector tube disposed in between.

Moreover, on an interior side 77 of the upper section 64, in the region of the end 69 in the position towards the transition 65, on opposing sides, bulges 78 and 79 are formed. Correspondingly, two such opposing bulges are also formed at analog location at the rear end 74. By these bulges 78, 79, the holding rail 7' is specifically held and guided in various operational phases during loading the lens into the loading chamber.

In the basic position shown in FIG. 14, the holding rail 7' is disposed below these bulges 78 and 79 viewed in vertical direction and thus in y-direction and contacted with the top 80 with these bulges 78 and 79.

As will be explained in more detail below, then, upon loading the lens 2 into the loading chamber, a relative movement between the support member 6' and the holding rail 7' is performed. Therein, only a vertical downward movement of the support member 6' is performed, in which the user especially uses the upper section 67 as a gripping member and then presses the support member 6' downwards. Therein, the holding rail 7' is then pushed past the bulges 78 and 79 and afterwards comes to rest above the bulges 78 and 79 in its end position viewed in vertical direction. In this position, then, the holding rail 7' is virtually prevented from slipping and the support member 6' from falling off upwards in undesired manner. In particular, legs 81 and 82 then seat on the bulges 78 and 79 as well as correspondingly on the opposing side on corresponding bulges.

Figure 15:
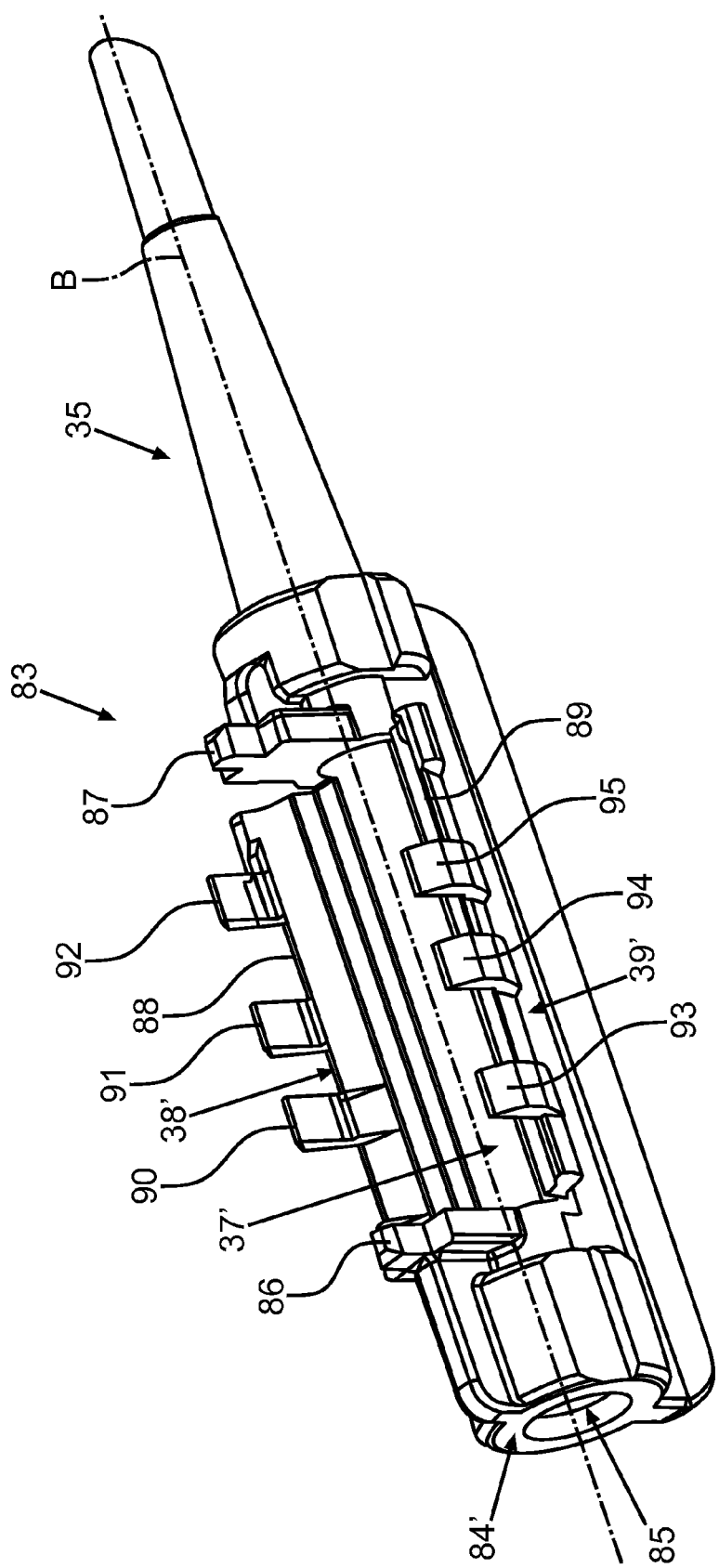
FIG. 15 a perspective representation of a further embodiment of a section of an injector tube with an insertion member and cover flaps of a loading chamber.

In FIG. 15, a perspective representation of an embodiment of a section 83 of an injector device 33' (FIG. 17) is shown. The section 83 includes the insertion member 35 and thus the tip, via which the lens 2 is brought into the eye. Moreover, the section 83 includes the loading chamber 37', into which the lens 2 is loaded after removing from the holding rail 7'. In this configuration, an injector tube 34' (FIG. 17) is thus constructed of two separate parts, which can be detachably assembled and again separated in non-destructive manner. With respect to that, a connecting region 84 is formed on the section 83. At this location, a plug connection or a locking connection or a bayonet connection or the like can be provided.

The piston 36 enters the loading chamber 37' via an opening 85 and then pushes the lens 2 loaded therein outwards through the insertion member 35.

These upwardly extending engaging members 86 and 87 are shown adjacent to the loading chamber 37', which engage with the receptacle 62 and 63 with the holding device 1' in the assembled state.

Moreover, in FIG. 15, cover flaps 38' and 39' are shown, wherein the completely opened state is illustrated in this respect. At free edges 88 and 89, plural gripping prongs 90, 91, 92 as well as 93, 94 and 95 formed spaced from each other are each formed. In the direction of the longitudinal axis B, the gripping prongs 90 to 92 are formed offset to the gripping prongs 93 to 95.

Figure 16:
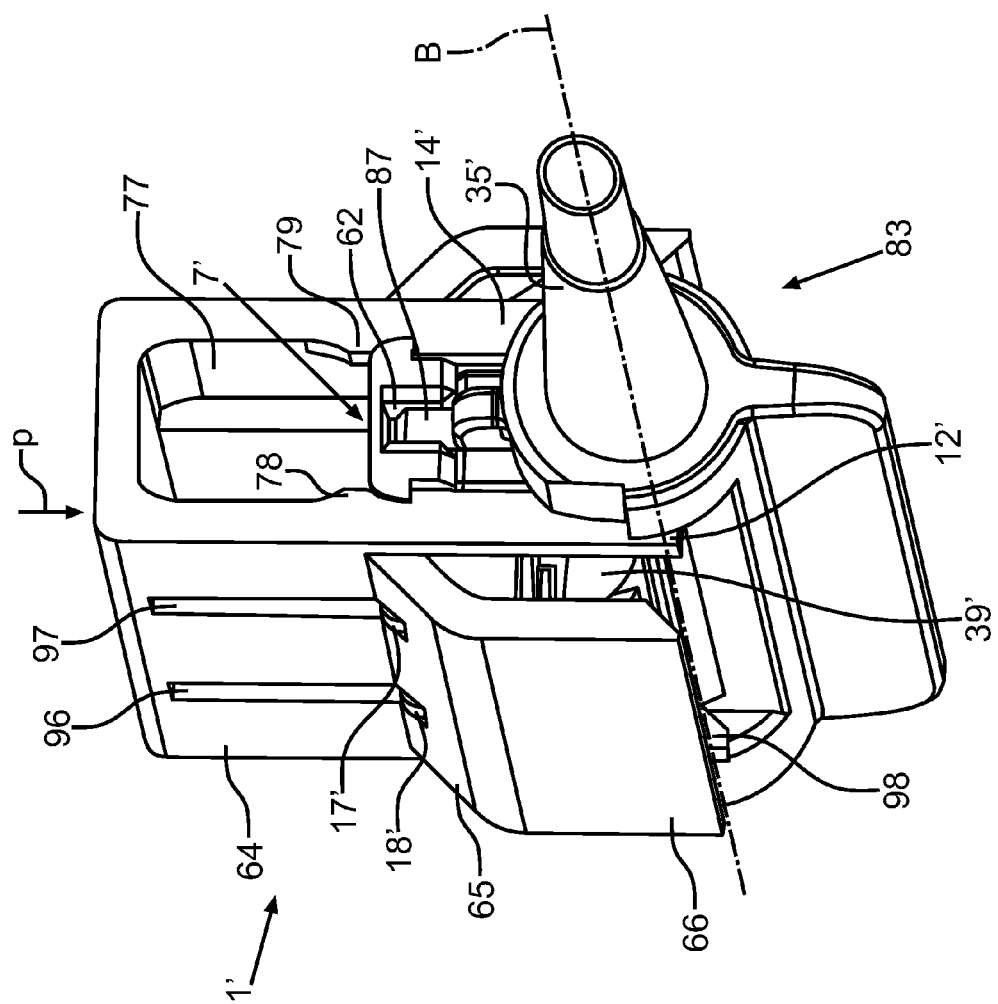
FIG. 16 a perspective representation of a holding device according to FIGS. 13 and 14, which is fitted onto the section according to FIG. 15.

In FIG. 16, in a perspective representation, the assembled state of the holding device 1' with the section 83 is shown in a basic position or in a starting position, respectively.

It can be provided that the holding device 1' according to the representation in FIG. 14 with the lens 2 attached to the holding rail 7' is positionally fixed disposed in the transport container 28 according to the representation in FIGS. 3 to 5. It can also be provided that with a configuration of the injector device 33' with a separable section 83 according to the representation in FIG. 15, an entire assembly as is shown in FIG. 16 is also disposed in the transport container 28 such that the section 83 is also loaded in the transport container 28 and is transported to the surgeon in this manner. There, by opening the transport container 28, the entire assembly according to FIG. 16 can then be removed and be attached to the other section of the injector tube 34'.

In FIG. 16, the slits 96 and 97 formed opposing the slits 67 and 68 shown in FIG. 14 are also shown. The holding device 1' is disposed positionally fixed on the section 83 along the axis B, wherein this is particularly effected by engagement of the engaging members 86, 87 with the receptacles 62 and 63, moreover by gripping around the section 83 at the outside by the guide members 12' and 14', wherein a further rear guide member 98 is also recognizable in FIG. 16.

Figure 17:
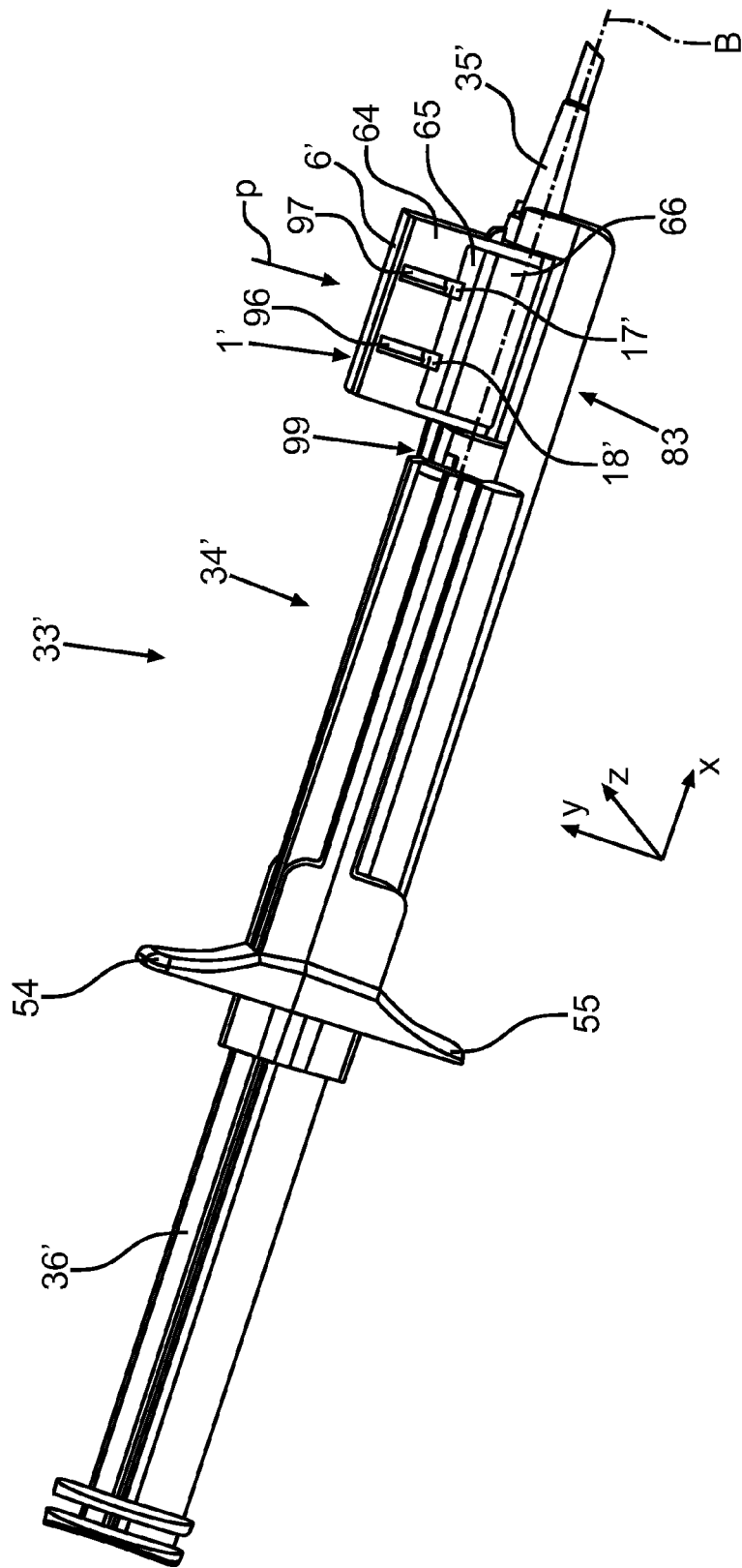
FIG. 17 a perspective representation of a further embodiment of an injector device.

In FIG. 17, the injector device 33' is shown in lateral perspective representation. Therein, the section 83 is connected to the remainder of the injector tube at the location 99 such that an entire injector tube 34' again results. For loading the lens 2 into the loading chamber 37', only a vertical movement of the support member in the direction of the arrow P (y-direction), but no movement in the direction of the axis B is effected in the shown embodiment.

Afterwards, it is now explained based on FIGS. 18 to 22, how the lens 2 is loaded into the loading chamber 37' starting from the basic state of the holding device 1' fitted on the section 83.

Figure 18:
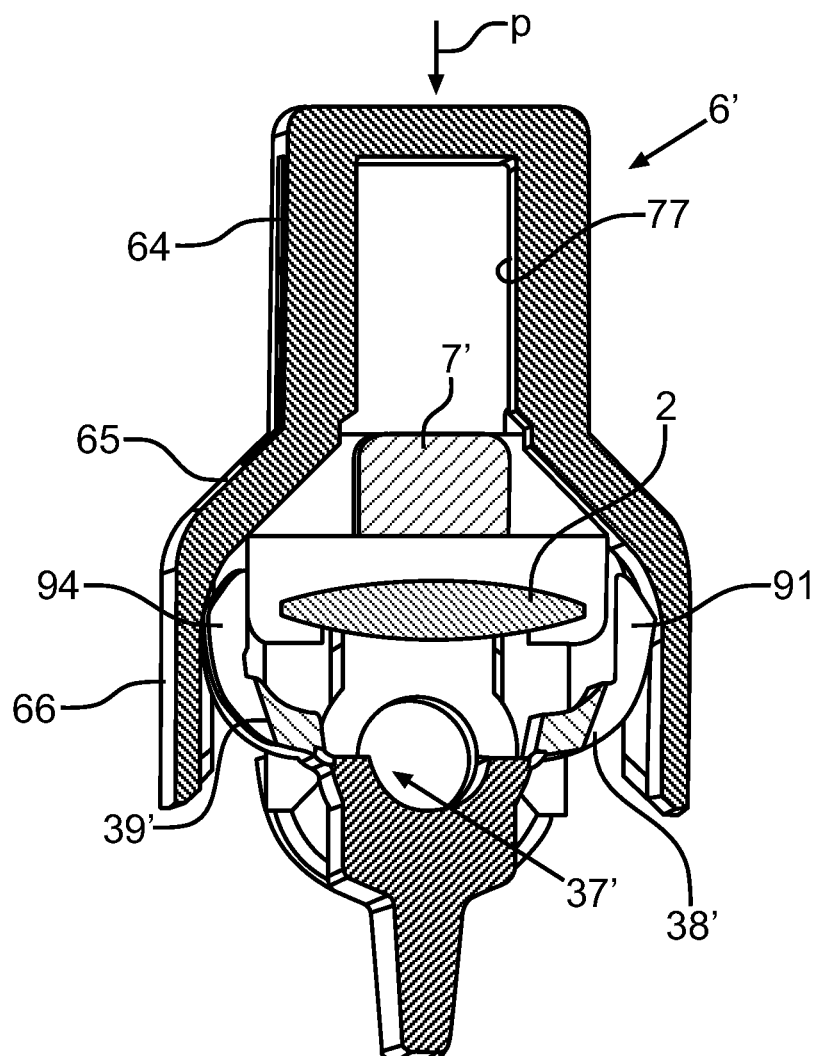
FIG. 18 a sectional representation through the injector device according to FIG. 17 in a first operational phase.

For this, in FIG. 18, a sectional representation in the y-z plane in FIG. 17 is shown. The cover flaps 38' and 39' are illustrated in the completely opened state, and the lens 2 is attached to the holding rail 7'. Starting from this state in FIG. 18, then, the support member 6' is pressed downwards in the direction of the arrow P. Since the holding rail 7' is positionally fixed attached to the section 83, thus, only a relative movement of the support member 6' to the holding rail 7' and the section 83 is performed.

Figure 19:
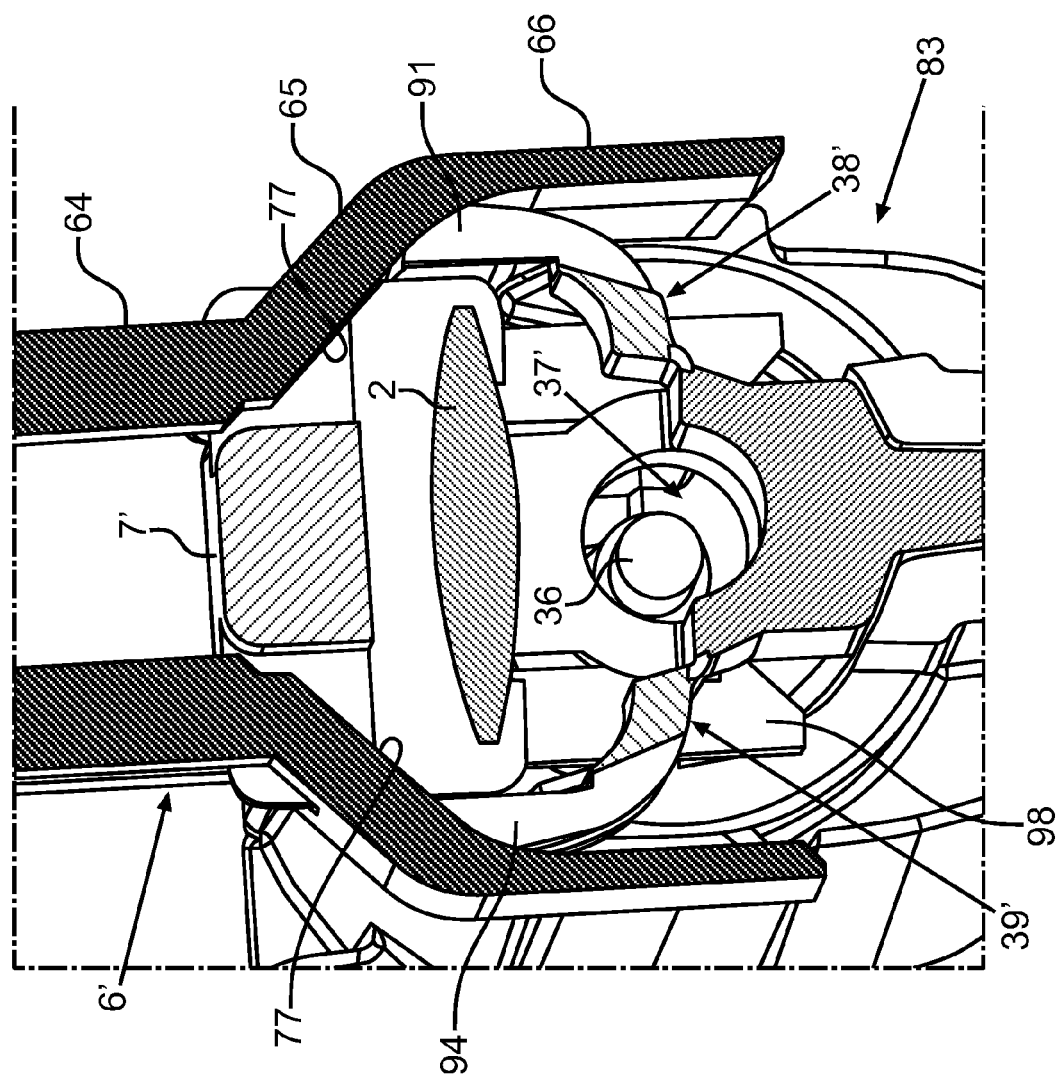
FIG. 19 a sectional representation through the injector device according to FIG. 17 in a second operational phase.

Therein, according to the further sectional representation in FIG. 19, an intermediate position is then reached, in which the gripping prongs 90 to 95 are mechanically contacted on the interior side 77 of the transition 65.

Due to the formation of the gripping prongs 90 to 95 as well as the stepless and continuously obliquely upwards extending interior side 77 at the transition 65, upon further downward movement of the support member 6' along the arrow P, a further intermediate state or a further intermediate position according to FIG. 2 is then achieved. Then, the cover flaps 38' and 39' are transferred from the completely open position into an intermediate closure position, wherein the edge 60 and the edge 61 of the lens 2 then are therein also mechanically contacted according to the representation in FIG. 20. This is correspondingly illustrated in FIG. 20. Starting from the state shown in FIG. 20, then, in a further operational phase and thus a further state according to the sectional representation in FIG. 21, the support member 6' is further vertically pressed down such that the cover flaps 38' and 39' are further moved towards each other and are further closed, and thereby the lens 2 is automatically folded. The position and the folding state of the lens 2 in FIG. 21 are only schematically illustrated, and in practice, this can substantially depart from that as well. With this representation, the automatic folding is only to be indicated symbolically.

Figure 22:
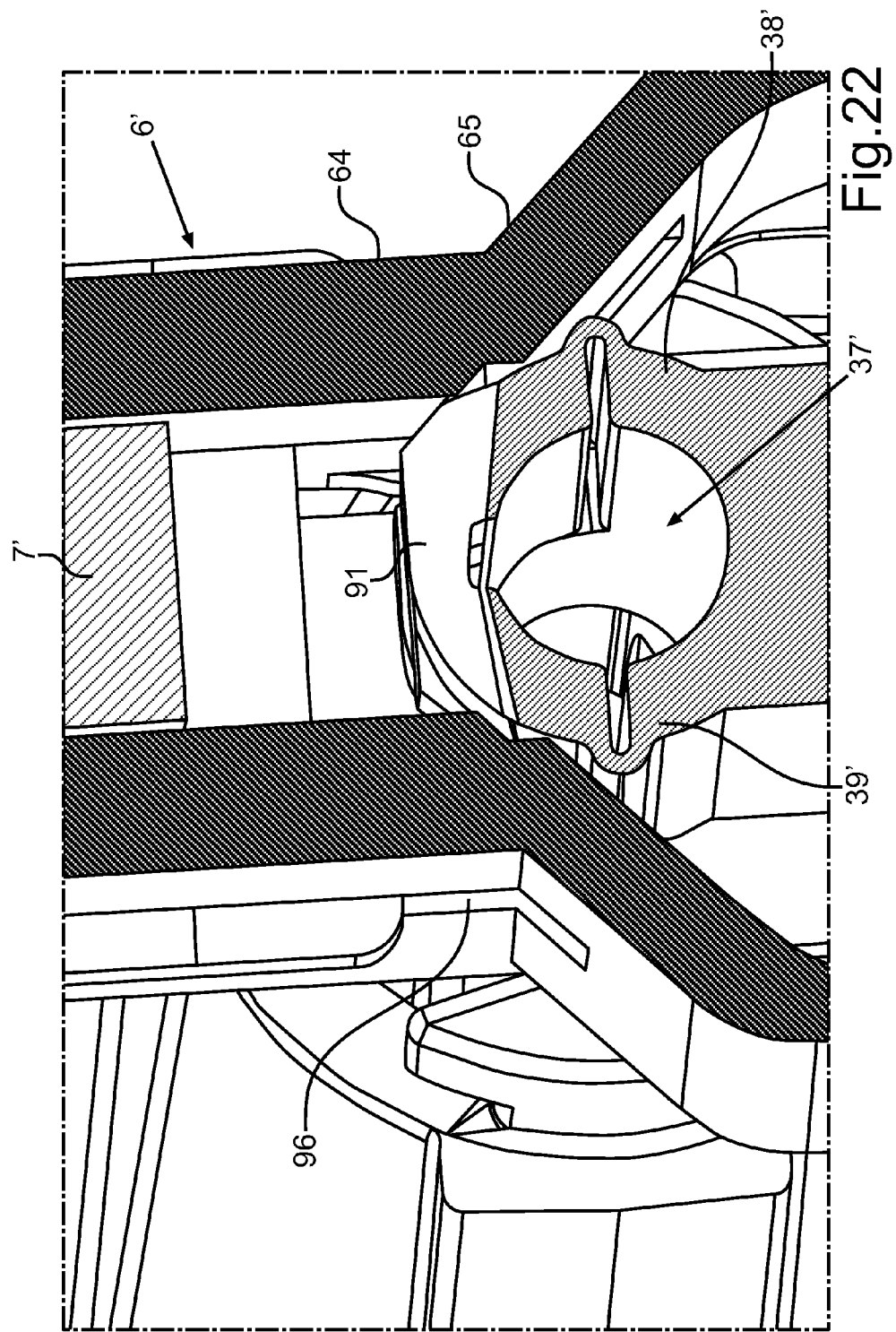
FIG. 22 a sectional representation through the injector device according to FIG. 17 in a fifth operational phase.

Upon further downward moving the support member 6' in the direction of the arrow P, then, according to the sectional representation in FIG. 22, the end state is shown, in which the lens 2 not shown in FIG. 22 is received in the loading chamber 37' and the cover flaps 38' and 39' are completely closed.

In this position, the holding rail 7 is then also disposed above the bulges 78 and 79 and retained there, and thereby, either the support member 6' cannot again fall down readily and simply.

Figure 20:
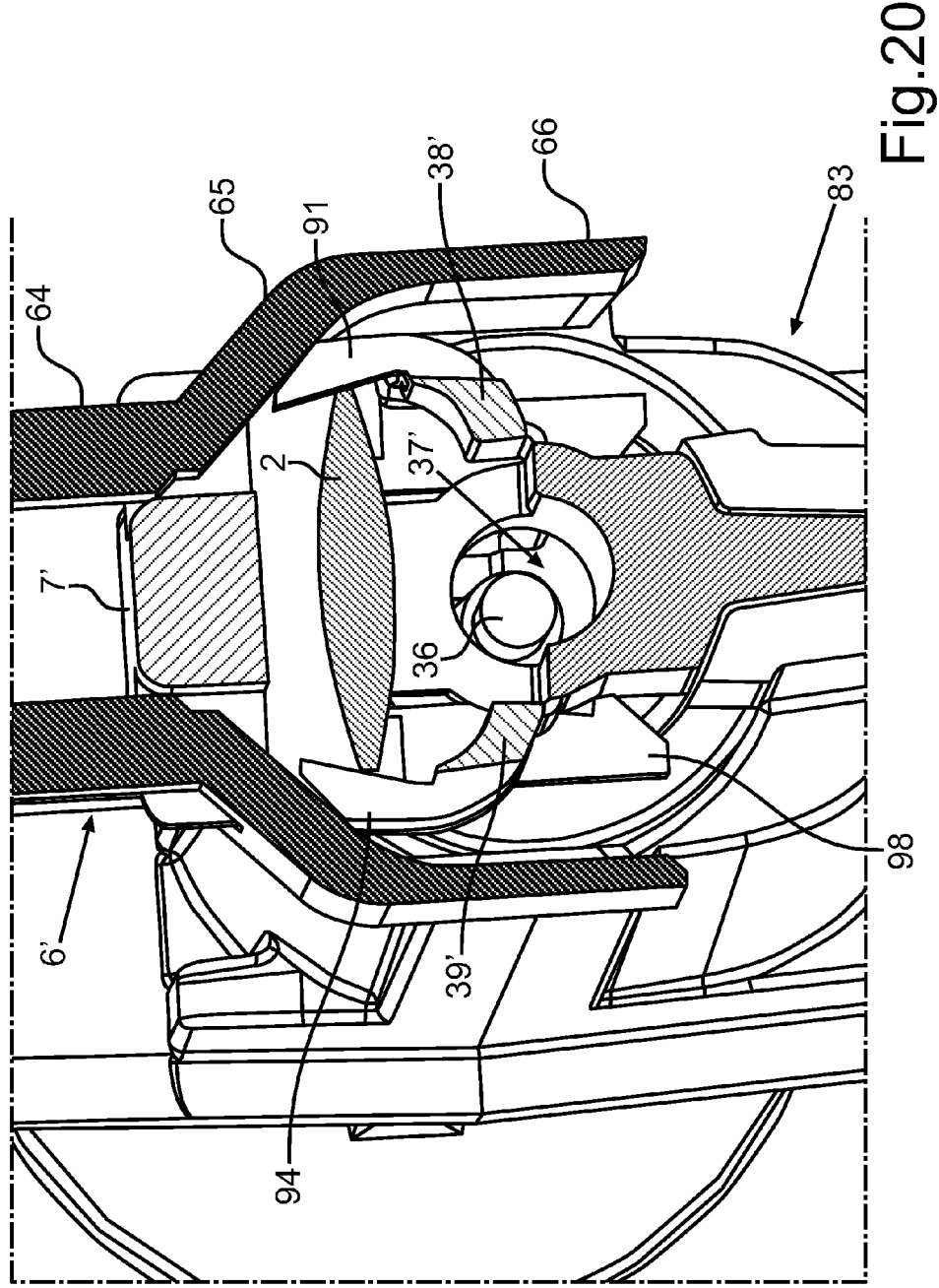
FIG. 20 a sectional representation through the injector device according to FIG. 17 in a third operational phase.
Figure 21:
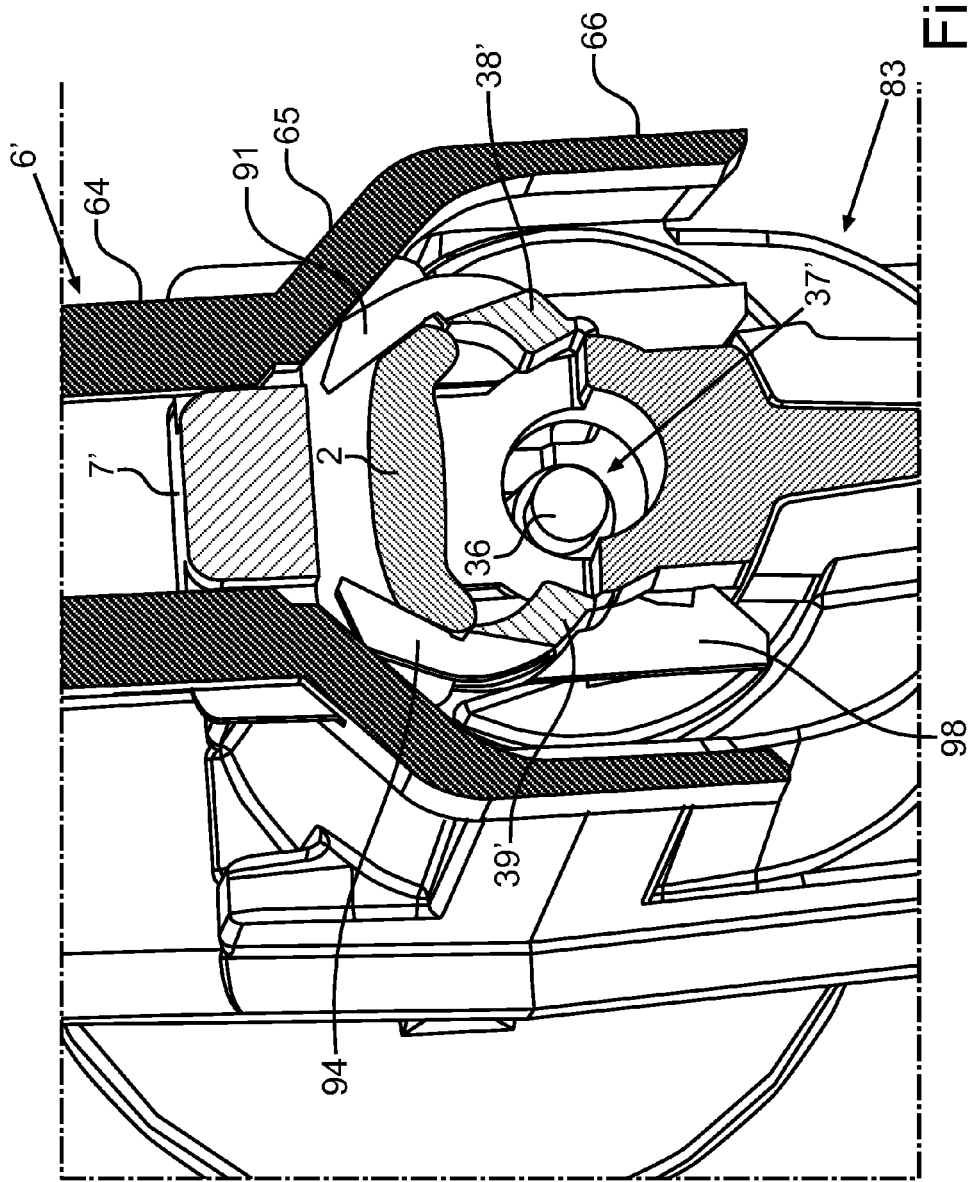
FIG. 21 a sectional representation through the injector device according to FIG. 17 in a fourth operational phase.

Starting from the position shown in FIGS. 20 and 21 or the intermediate states, respectively, by the further movement of the cover flaps 38' and 39' towards each other, the lens 2 is also automatically removed from the holding rail 7'.

Below, a summary of advantages of the invention and embodiments thereof:

It folds and compresses the IOL before the IOL is moved forward in the lumen by the plunger. This is necessary for micro-incision surgery (MICS). If the lens is not folded and compressed at the time the plunger engages the lens, the plunger must capture the lens positively and control the lenses forward movement into the lumen. This is best accomplished with a hard-tipped plunger that has an open fork (or jaw) that captures the lens edge. Unfortunately, the tip of the actual injector has to be very small for MICS surgical techniques. A hard-tipped plunger that has a small enough "face" to pass through the very small lumen required for MICS techniques cannot reliably grasp the lens edge when the lens is not compressed. In addition, such a plunger will exert greater pressure per unit area on the lens, likely resulting in lens damage. The alternative is the use of a soft-tip plunger. However, here the problem is that such a plunger cannot easily grasp and positively control the lens when it is unfolded and uncompressed. In contrast, when the lens is folded and compressed, it is possible to utilize a soft-tip plunger that will push easily and gently against the bulk of the lens. As the lens is packed into the lumen, it is not possible for the piston to bypass the lens. It is also not necessary to capture and positively guide the lens.

It separates all portions of the lumen from the IOL's sterile container. This is beneficial for a number of very important reasons:

Reason 1: The IOL, in the fluid-filled container, must be steam sterilized. The injectors are typically ETO gas sterilized. The steam sterilization process is very damaging to the lubricious coatings that are necessary to permit the lens to reliably pass through the very small lumen. As a consequence, if any portion of the lumen is inside the IOL's container, this portion will not have the ideal, lubricious coating.

Reason 2: in general terms, it is preferable to package the IOL in very simple, basic materials. This eliminates long-term exposure of the lens to any materials other than those that are essential to accomplish the simple task of containing the lens and fluid and holding and protecting the lens. In a preferred embodiment, this means that the lens and solution would only be exposed to pure polypropylenes and polyimides, without additives.

Reason 3: There is a phenomenon observed with acrylic lenses: they tend to stick to other surfaces (and to themselves). When a lens is packaged inside a portion of the lumen, the movement of the lens can be unpredictable due to tendencies of the lens to stick to surfaces inside the lumen. This can be resisted by applications of coatings or additives to the portion of the lumen containing the lens. In the SLC (Shuttle Retainer Concept) which is the system 1 or 1', the lens is stored inside a separate component (the shuttle-retainer) and is then mechanically transferred to the loading chamber of the injector. This process of mechanical transfer removed the sticking problems from the lens-delivery process. The lens is not in a static position inside the lumen of the injector for a long enough period of time to stick to the lumen. In addition, the lubricious coating of the lumen will be in optimal condition as mentioned previously. This eliminates any possibility of IOL sticking in the lumen.

The mechanical transfer of the IOL from its storage container to the injector is another differentiating factor to prior art and in terms of the way it is actually achieved, is probably one of the more unique aspects of the SLC design. This mechanical transfer has the following benefits:

It is a means of ameliorating the lens sticking problem mentioned above.

It requires a significant reduction in the manual manipulation of the system as a whole in order to prepare the system for use. Not only in terms of operational steps to be performed by the end-user, but also in terms of the complexity of the individual operations and the opportunities for variation and error.

By eliminating the need to manipulate the lens directly (e.g. grasp the IOL directly with forceps), it reduces opportunities for lens damage and/or contamination. This improves the potential for success of the procedure itself: less risk of reduced lens performance due to damage to optical surfaces or support structures and less risk of patient infection, inflammation, or injury due to contamination of the lens during handling.

In a similar fashion, the mechanical closure of the loading chamber of the injector is superior to existing means of manually performing these tasks. It eliminates potential variation and error, and reduces the number of steps and their complexity.

The invention claimed is:

1. A holding device for an intraocular lens, wherein the holding device is formed open to the bottom and has an elongated support member open to the bottom, on which an elongated holding rail for holding the lens is disposed, the elongated support member extending along a longitudinal axis and including a gripping member positioned on the top of the holding device and which is configured for gripping by a user, wherein the support member and the holding rail are disposed against each other and movable with respect to each other, the support member having a base body open to the bottom, on which a support arm extending parallel to the longitudinal axis is respectively disposed on opposing sides of the longitudinal axis of the support member, wherein on facing interior sides of the support arms, on each support arm, at least one guide member is respectively disposed, wherein each guide member is formed for engagement with a cover flap of an injector device covering a loading space.

2. The holding device according to claim 1, wherein the holding rail is movable upwards and downwards along or parallel the longitudinal axis of the support member and/or perpendicularly to the longitudinal axis.

3. The holding device according to claim 1, wherein the lens, in its loading position on the holding rail, is disposed on a bottom side of the holding rail and is disposed in the holding device freely accessible through the support member open at the bottom.

4. The holding device according to claim 3, wherein the lens is freely accessible on both sides laterally and from below in its loading position on the holding rail.

5. The holding device according to claim 1, wherein on a lower border of the base body and/or a lower border of at least one support arm, a positioning member is disposed, by which the holding device can be fixedly attached in a transport container.

6. The holding device according to claim 1, wherein the holding device is formed in one piece.

7. The holding device according to claim 1, wherein the support member and the holding rail are separate parts.

8. The holding device according to claim 1, wherein the support member is elongated and clamp-like and is widened to the bottom.

9. The holding device according to claim 8, wherein the support member has an upper narrow section and a lower wide section, and an expanding transition is formed between the sections.

10. The holding device according to claim 9, wherein the upper section and the transition have slits, which are formed for receiving and guiding the holding rail.

11. The holding device according to claim 9, wherein at least one bulge is respectively formed on the facing interior sides of the upper section and/or the guide members at the transition.

12. The holding device according to claim 11, wherein the holding rail is movable in vertical direction relatively to the support member, and the holding rail is disposed in a starting position below the bulges and is disposed in an end position above the bulges and is held by the bulges above them.

13. The holding device according to claim 8, wherein guide members extend downwards on opposing sides of the upper section, and a receiving space is formed between a guide member and a wall of the lower section.

14. The holding device according to claim 8, wherein the holding rail has a receptacle, respectively, at a front end and a rear end at the bottom, with which an engaging member formed in the region of a loading chamber of an injector device respectively engages in the assembled state.

15. A holding device for an intraocular lens, the holding device comprising:

an elongated support member extending along a longitudinal axis, the elongated support member being open to a bottom side and including support arms adjacent a hole in the support member, the hole extending from at least a portion of a top side of the elongated support member to the bottom side of the elongated support member;

an elongated holding rail coupled to the elongated support member and configured for holding the intraocular lens; and a gripping member positioned on the top side of the elongated support member which is configured for gripping by a user, wherein the elongated support member and the elongated holding rail are separate parts disposed against each other and movable with respect to each other.

16. A holding device for an intraocular lens, the holding device comprising:
- an elongated support member extending along a longitudinal axis, the elongated support member including a hole extending between a top side and a bottom side of the holding device;
- an elongated holding rail coupled to the elongated support member and configured for holding the intraocular lens; and
- a gripping member positioned on the top side of the elongated support member which is configured for gripping by a user,
- wherein the elongated holding rail is accessible via the opening through the top side and the bottom side of the holding device and wherein the elongated support member and the elongated holding rail are separate parts.

* * * * *